US008479341B2

(12) United States Patent
Iwahori

(10) Patent No.: US 8,479,341 B2
(45) Date of Patent: Jul. 9, 2013

(54) ELECTRIC TOOTHBRUSH

(75) Inventor: Toshiyuki Iwahori, Mishima-gun (JP)

(73) Assignee: Omron Healthcare Co., Ltd., Muko (JP)

( * ) Notice: Subject to any disclaimer, the term of this patent is extended or adjusted under 35 U.S.C. 154(b) by 0 days.

(21) Appl. No.: 13/491,189

(22) Filed: Jun. 7, 2012

(65) Prior Publication Data
US 2012/0266397 A1    Oct. 25, 2012

Related U.S. Application Data

(63) Continuation of application No. PCT/JP2011/050033, filed on Jan. 5, 2011.

(30) Foreign Application Priority Data

Jan. 8, 2010  (JP) ................................. 2010-003110

(51) Int. Cl.
A46B 9/04    (2006.01)
(52) U.S. Cl.
USPC .......................................................... 15/22.1
(58) Field of Classification Search
USPC ....................................... 15/22.1, 22.2, 167.1
See application file for complete search history.

(56) References Cited

U.S. PATENT DOCUMENTS

| 7,464,430 | B2 * | 12/2008 | Filsouf ............................ 15/22.1 |
| 2006/0037197 | A1 | 2/2006 | Hawes et al. |
| 2008/0280248 | A1 * | 11/2008 | Pitts et al. ........................ 433/32 |
| 2009/0092955 | A1 | 4/2009 | Hwang |
| 2009/0130636 | A1 | 5/2009 | Hwang |
| 2009/0211042 | A1 * | 8/2009 | Bock .............................. 15/22.1 |
| 2009/0291422 | A1 * | 11/2009 | Puurunen et al. ............. 434/263 |

FOREIGN PATENT DOCUMENTS

| JP | A-2005-152217 | 6/2005 |
| JP | A-2006-520212 | 9/2006 |
| JP | A-2008-543418 | 12/2008 |
| JP | A-2009-222704 | 10/2009 |
| JP | A-2009-240759 | 10/2009 |
| JP | A-2009-240760 | 10/2009 |
| JP | A-2009-273621 | 11/2009 |
| JP | A-2009-285416 | 12/2009 |
| JP | A-2009-291316 | 12/2009 |
| WO | WO 2009/104608 A1 | 8/2009 |
| WO | WO 2009/113491 A1 | 9/2009 |
| WO | WO 2009/113492 A1 | 9/2009 |
| WO | WO 2009/148018 A1 | 12/2009 |

* cited by examiner

OTHER PUBLICATIONS

Apr. 12, 2011 International Search Report issued in International Patent Application No. PCT/JP2011/050033.

Primary Examiner — Robert Scruggs
(74) Attorney, Agent, or Firm — Oliff & Berridge, PLC

(57) ABSTRACT

An electric toothbrush includes bristles, a bristle driving unit, an orientation detection sensor, and an electrode-based contact detection unit for detecting contact with a body. The contact detection unit includes a first detection unit for detecting contact with or proximity to a rear surface side of a brush portion. The electric toothbrush detects orientation information based on an output from the orientation detection sensor, and estimates a brushing area based on at least the orientation information. In the area estimation, in the case where the brushing area determined based on the orientation information is a dentition surface on a right buccal side or a left lingual side or a dentition surface on a left buccal side or a right lingual side, it is determined whether the brushing area corresponds to the buccal side or the lingual side based on an electric signal obtained from the first detection unit.

13 Claims, 42 Drawing Sheets

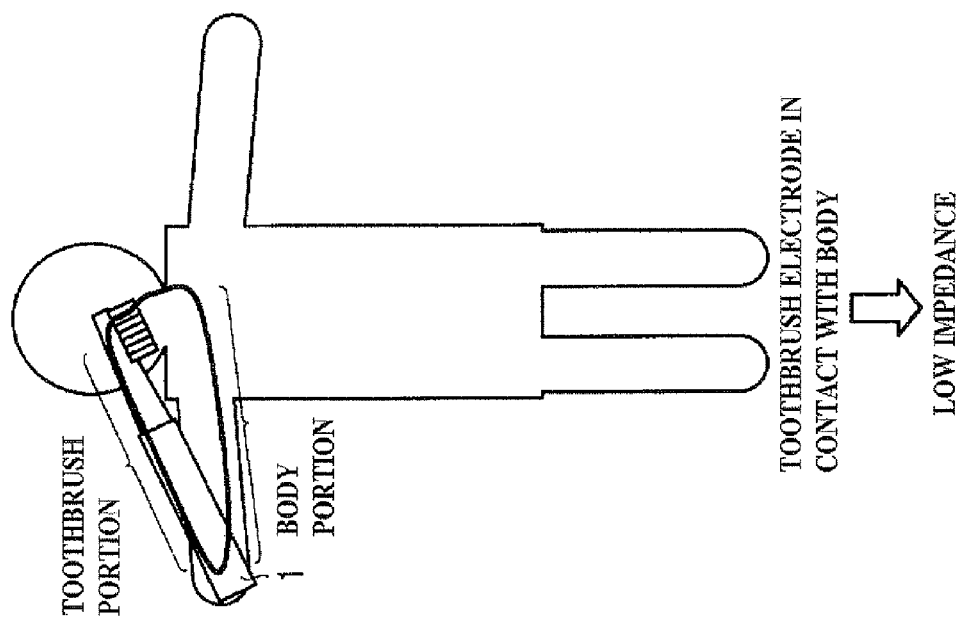
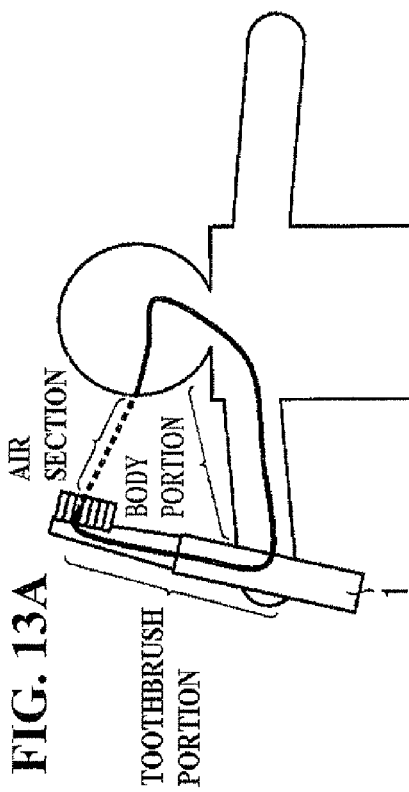

FIG. 18

| AREA | BRUSHING TIME (SEC) | BRUSH ANGLE (DEG) | BRUSH PRESSURE (g) | BRUSHING INDEX |
|---|---|---|---|---|
| MAXILLARY ANTERIOR BUCCAL SIDE | 7.5 | 70 | 120 | 78 |
| MAXILLARY ANTERIOR LINGUAL SIDE | – | – | – | – |
| MAXILLARY LEFT BUCCAL SIDE | 12.2 | 45 | 108 | 100 |
| MAXILLARY LEFT LINGUAL SIDE | – | – | – | – |
| MAXILLARY RIGHT BUCCAL SIDE | – | – | – | – |
| MAXILLARY RIGHT LINGUAL SIDE | – | – | – | – |
| MANDIBULAR ANTERIOR BUCCAL SIDE | – | – | – | – |
| MANDIBULAR ANTERIOR LINGUAL SIDE | – | – | – | – |
| MANDIBULAR LEFT BUCCAL SIDE | 2.0 | 53 | 95 | 25 |
| MANDIBULAR LEFT LINGUAL SIDE | – | – | – | – |
| MANDIBULAR RIGHT BUCCAL SIDE | – | – | – | – |
| MANDIBULAR RIGHT LINGUAL SIDE | – | – | – | – |

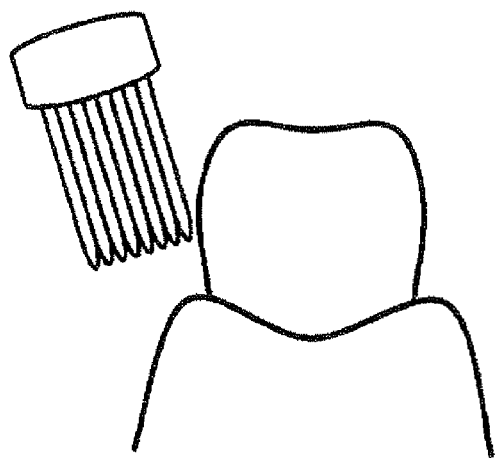
FIG. 19A 【15°】
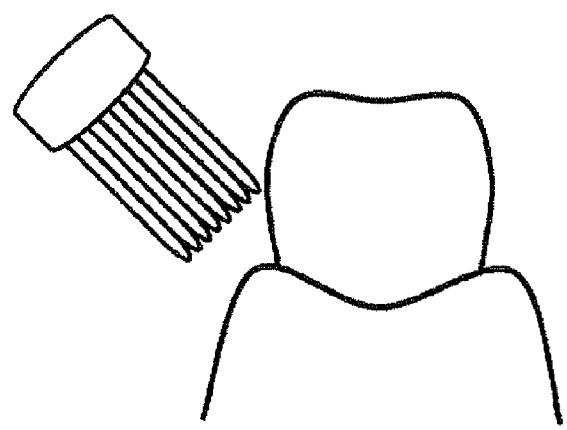
FIG. 19B 【45°】
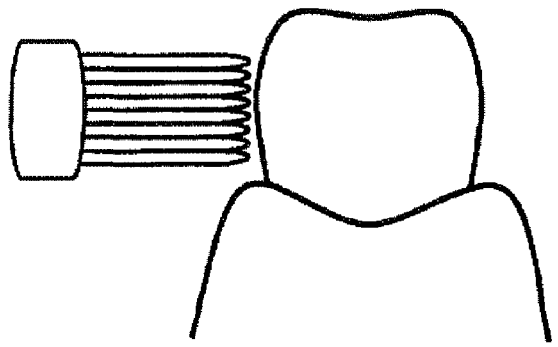
FIG. 19C 【90°】

ELECTRIC TOOTHBRUSH

This is a Continuation of International Application No. PCT/W2011/050033 filed Jan. 5, 2011, which claims the benefit of Japanese Patent Application No. 2010-003110 filed Jan. 8, 2010. The disclosure of the prior applications is hereby incorporated by reference herein in its entirety.

TECHNICAL FIELD

The present invention relates to electric toothbrushes, and particularly relates to electric toothbrushes that are capable of estimating a brushing area.

BACKGROUND ART

Some toothbrushes are provided with functions for estimating a brushing area by calculating trajectories through the use of accelerometers, gyroscopes, or the like.

For example, JP-2009-240760A (Patent Citation 1) and JP-2009-240759A (Patent Citation 2) disclose estimating a brushing area using an accelerometer. These patent citations furthermore disclose using a camera, a temperature sensor, or a distance sensor to determine whether a surface is, for example, the buccal-side surface of the lower-left jaw or the lingual-side surface of the lower-right jaw.

CITATION LIST

Patent Literature

Patent Citation 1: JP-2009-240760A
Patent Citation 2: JP-2009-240759A

SUMMARY OF INVENTION

Technical Problem

When detecting a brushing area, the toothbrush main body has a similar orientation (that is, the direction in which the brush surface faces) when positioned at, for example, the buccal-side surface of the lower-left jaw and at the lingual-side surface of the lower-right jaw. It has thus been necessary to determine the brushing area from trajectory information indicating trajectories traced by the toothbrush during brushing, or by using a camera, a temperature sensor, or a distance sensor as mentioned above.

Determining whether an area is on the buccal side or on the lingual side based on trajectory information of the toothbrush main body requires a high-performance computational processing unit. On the other hand, cameras, temperature sensors, and distance sensors are, depending on the manner in which they are provided in the toothbrush, susceptible to being soiled, and can also result in complicated wiring schemes.

Having been achieved in order to solve problems such as those mentioned above, it is an object of the present invention to provide an electric toothbrush that is capable of accurately estimating a brushing area using a simple configuration.

Solution to Problem

An electric toothbrush according to an aspect of the invention includes bristles, a driving unit for driving the bristles, an orientation detection sensor for detecting the orientation of the electric toothbrush, an electrode-based contact detection unit for detecting contact with a body, a detection unit for detecting orientation information of the electric toothbrush based on an output from the orientation detection sensor, and an area estimation unit for estimating a brushing area based on at least the orientation information. The contact detection unit has a first detection unit for detecting contact with or proximity to a rear surface side of a brush portion in which the bristles are disposed. The area estimation unit has a determination unit for determining, in the case where the brushing area determined based on the orientation information is a dentition surface on a right buccal side or a left lingual side or a dentition surface on a left buccal side or a right lingual side, whether the brushing area corresponds to the buccal side or the lingual side based on an electric signal obtained from the first detection unit.

Preferably, the determination unit calculates the percentage of time for which the rear surface side of the brush portion is in contact with the body based on the output of the first detection unit, and determines that the brushing area corresponds to the buccal side if the calculated percentage of time is greater than or equal to a predetermined percentage and determines that the brushing area corresponds to the lingual side if the calculated percentage of time is less than the predetermined percentage.

Preferably, the first detection unit has an electrode disposed on the rear surface side of the brush portion, and the determination unit determines whether or not contact is made with the body by detecting the magnitude of the impedance of the electrode.

Preferably, the first detection unit further has an electrode disposed on a main body portion of the electric toothbrush.

Alternatively, it is desirable for the first detection unit to have an electrostatic capacitance-type detection unit, that has an electrode, disposed on the rear surface side of the brush portion; and for the determination unit to determine contact with or proximity to the body by detecting changes in the electrostatic capacitance of the electrostatic capacitance-type detection unit.

Preferably, the contact detection unit further has a second detection unit for detecting contact with a location that is not the rear surface of the brush portion but is a location that can enter into the mouth during brushing; and the electric toothbrush further includes a detailed area detection unit for detecting, based on an electrical signal obtained from the second detection unit, a more detailed area than the brushing area estimated by the area estimation unit.

Preferably, the second detection unit detects contact with a shank portion; and the detailed area detection unit detects, in the case where the estimated brushing area corresponds to the back teeth, a detailed area of the back teeth by detecting whether or not the second detection unit has come into contact with the body.

Alternatively, it is desirable for the second detection unit to detect contact with the tip of the brush portion; and for the detailed area detection unit to detect, in the case where the estimated brushing area corresponds to the front teeth, a detailed area of the front teeth by detecting whether or not the second detection unit has come into contact with the body.

Preferably, the contact detection unit further has a second detection unit for detecting contact with a side surface of the brush portion; and the electric toothbrush further includes an area correction unit for correcting, based on an electrical signal obtained from the second detection unit, the brushing area estimated by the area estimation unit.

Preferably, the electric toothbrush further includes an infrared sensor, disposed on the brush surface of the brush portion, for detecting a temperature, and an identification unit for identifying, based on an output from the infrared sensor, whether the teeth or the gums are being brushed.

Preferably, the electric toothbrush further includes an optical sensor provided in a location that enters into the oral cavity when brushing the back teeth, and an area correction unit for correcting the brushing area estimated by the area estimation unit by determining whether the area being brushed corresponds to front teeth or back teeth based on a signal obtained from the optical sensor.

Preferably, the electric toothbrush further includes a measurement unit for measuring a brushing time for each brushing area estimated by the area estimation unit, and an output unit for outputting a brushing result based on a result of measuring the brushing time.

Preferably, the electric toothbrush further includes a mode switching unit for switching an operating mode of the driving unit in accordance with the brushing area estimated by the area estimation unit.

Advantages Effects of Invention

According to the present invention, in the case where the brushing area determined based on the orientation information obtained through the output from the orientation detection sensor corresponds to the right buccal-side dentition surface or left lingual-side dentition surface, or to the left buccal-side dentition surface or right lingual-side dentition surface, whether the brushing area is on the buccal side or on the lingual side can be determined using the electrode-based contact detection unit. Therefore, brushing areas can be estimated with a high level of precision using a simple configuration.

BRIEF DESCRIPTION OF DRAWINGS

FIGS. 13A and 13B are diagrams schematically illustrating a circuit passing through a body according to the first embodiment, and illustrate a state in which a rear surface electrode is in contact with the body and a state in which the rear surface electrode is not in contact with the body.

FIG. 18 is a diagram illustrating an example of brushing information.

FIGS. 19A, 19B, and 19C are diagrams illustrating brush angles.

DESCRIPTION OF EMBODIMENTS

Figure 1:
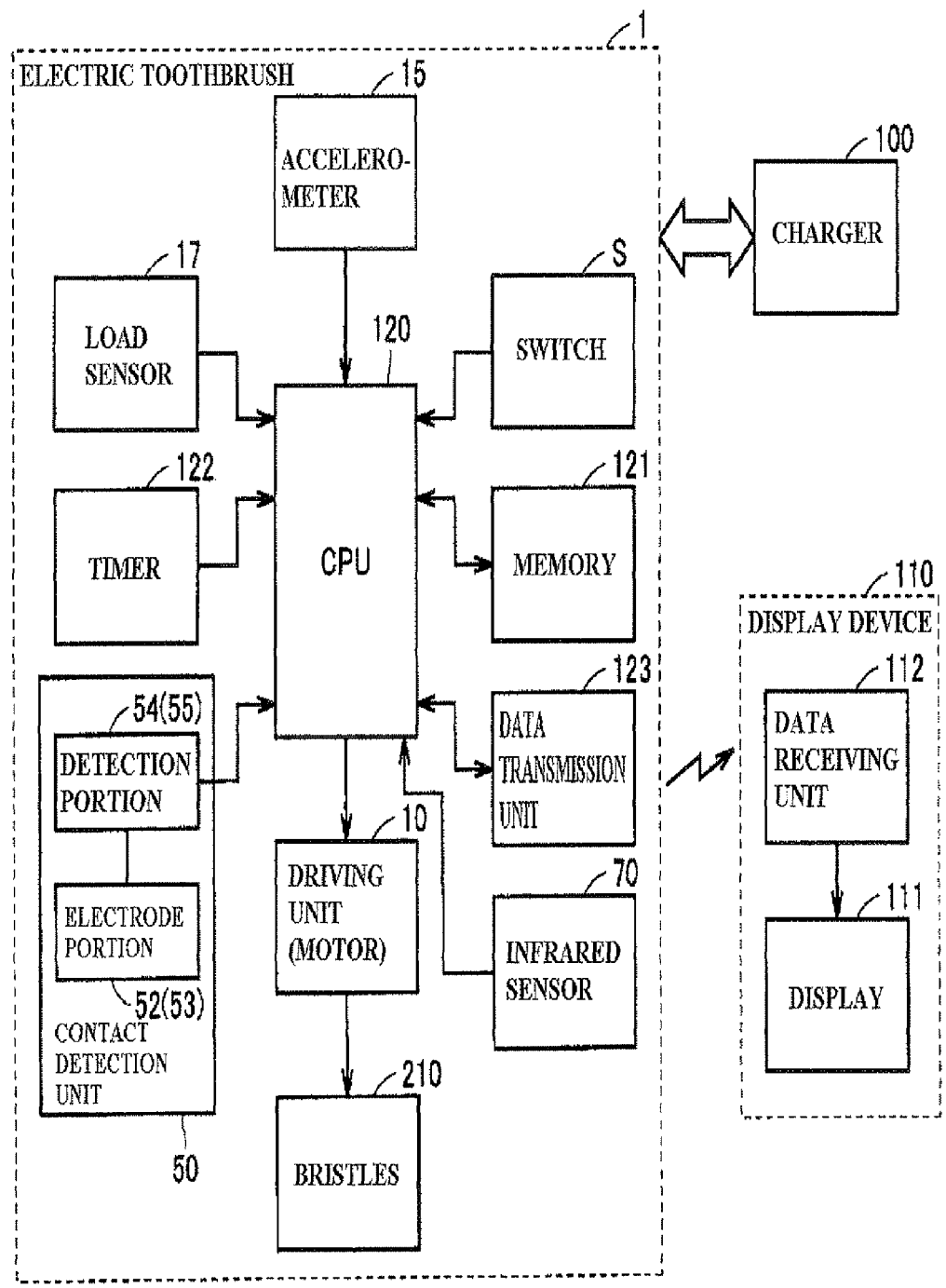
FIG. 1 is a block diagram illustrating a display system including an electric toothbrush according to a first embodiment.

Embodiments of the present invention will be described hereinafter with reference to the drawings. Note that identical or corresponding areas of the drawings will be assigned the same reference numerals, and descriptions thereof will not be repeated.

First Embodiment

Configuration

The configuration of an electric toothbrush will be described with reference to FIGS. 1 through 4.

Figure 2:
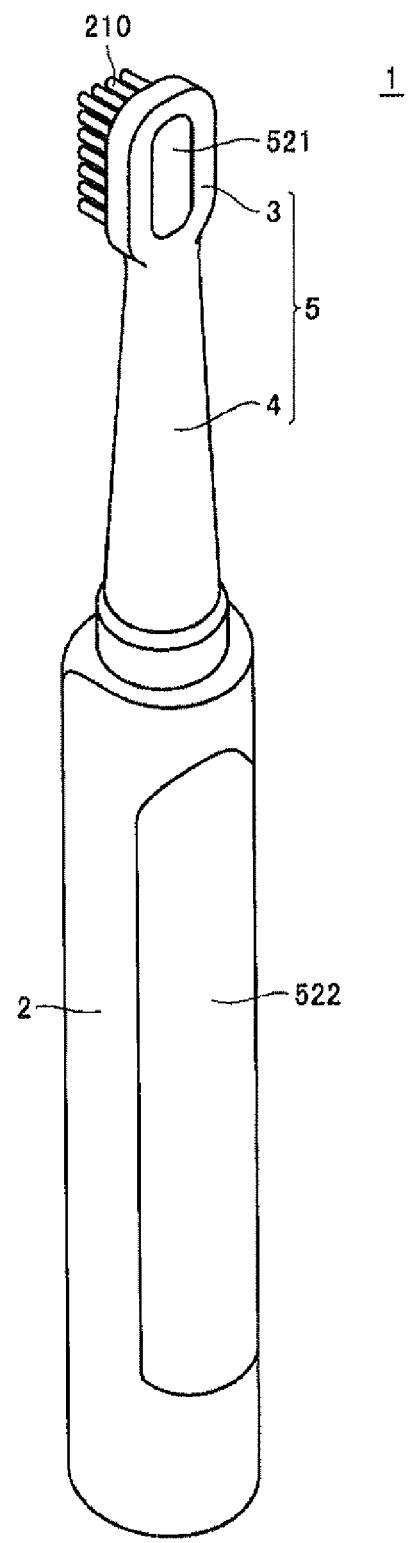
FIG. 2 is a perspective view illustrating an example of the external appearance of the electric toothbrush according to the first embodiment.
Figure 3:
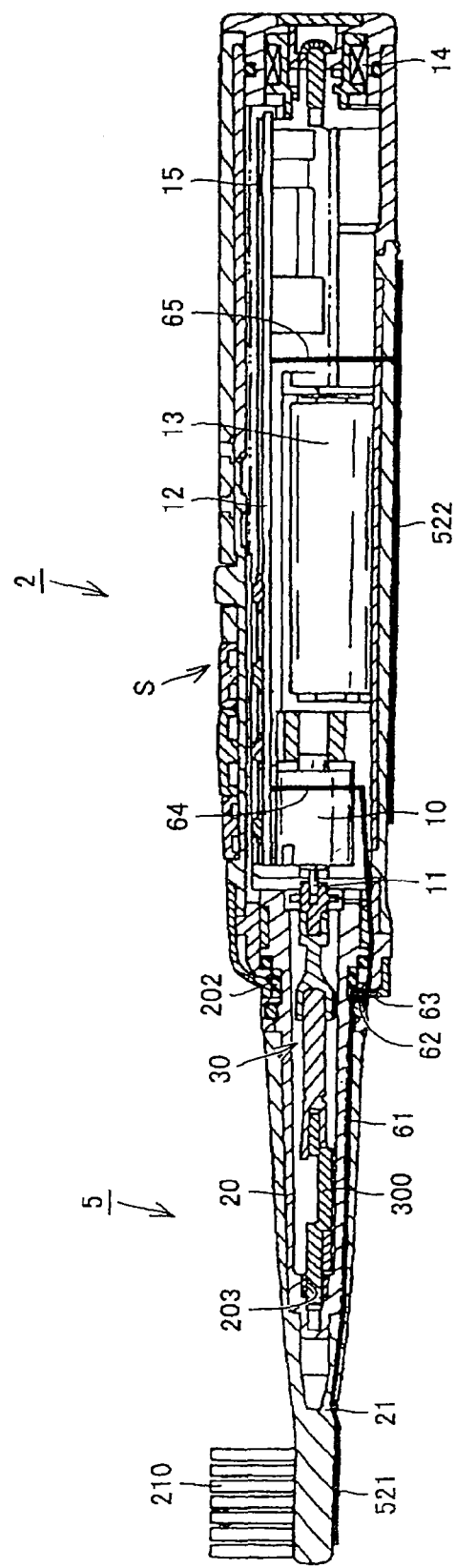
FIG. 3 is a cross-sectional view illustrating an example of the internal configuration of the electric toothbrush according to the first embodiment.
Figure 4:
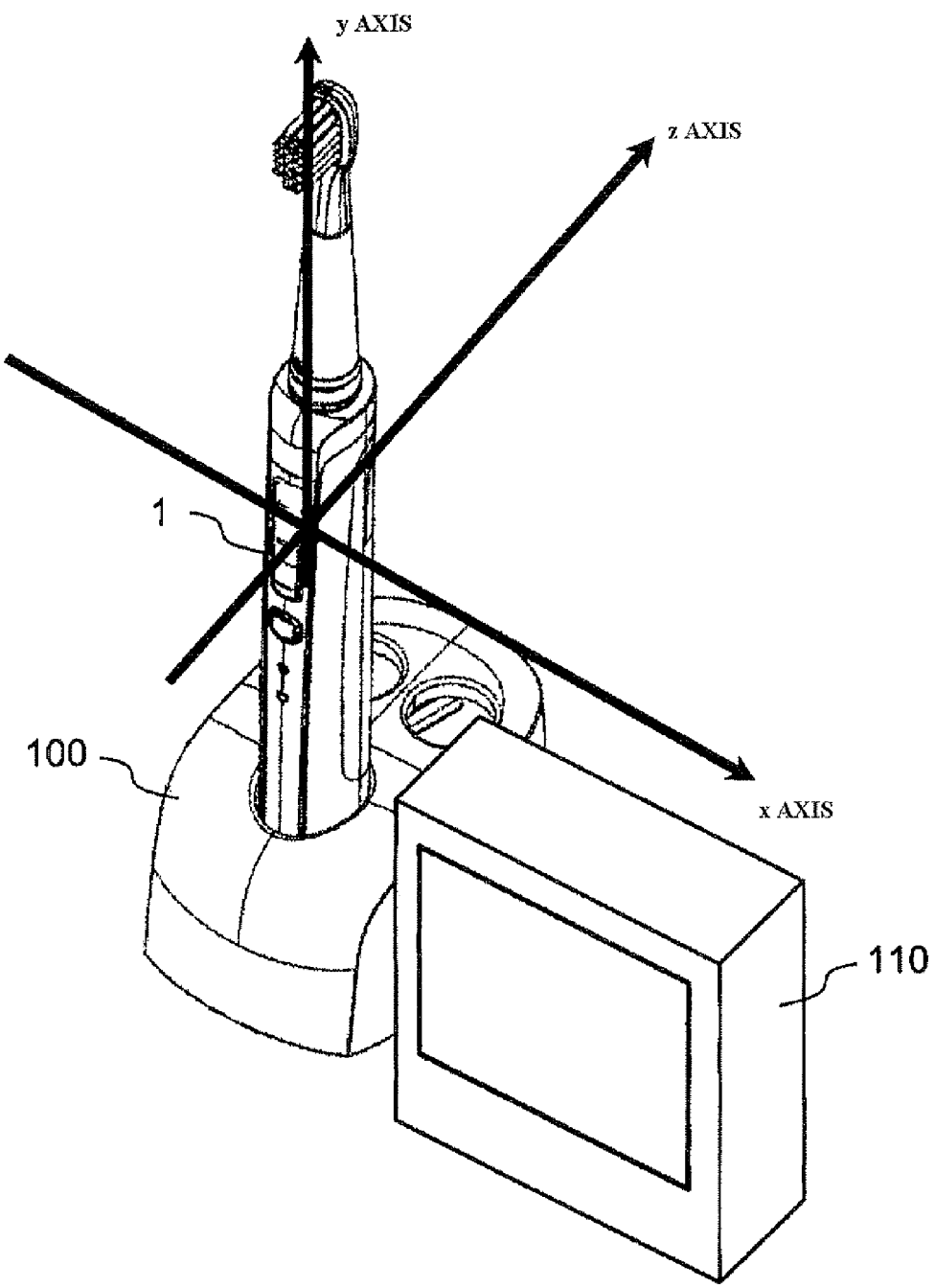
FIG. 4 is a perspective view illustrating an example of the external appearance of the display system including the electric toothbrush according to the first embodiment.

FIG. 1 is a block diagram illustrating a display system including an electric toothbrush according to the first embodiment, whereas FIG. 2 is a perspective view illustrating an example of the external appearance of the electric toothbrush. FIG. 3 is a cross-sectional view illustrating an example of the internal configuration of the electric toothbrush according to the first embodiment, whereas FIG. 4 is a perspective view illustrating an example of the external appearance of the display system including the electric toothbrush.

An electric toothbrush 1 includes a main body portion 2 (also called simply a "main body 2" hereinafter) that includes a motor 10 serving as a driving source, and a vibrating member 5 that vibrates as a result of the driving of the motor 10. The main body 2 has an overall cylindrical shape, and also functions as a handle portion that a user grips with his/her hand when brushing his/her teeth.

Furthermore, the electric toothbrush 1 according to the present embodiment includes a charger 100, in which the main body 2[0] is mounted, for charging the electric toothbrush 1, and a display device 110 for outputting a brushing result.

A switch S for turning the power on and off and for switching between operating modes is provided in the main body 2. The motor 10 that serves as a driving source, a driving circuit 12, a chargeable battery 13 that serves as a 2.4 V power source, a charging coil 14, and so on are provided within the main body 2. When charging the chargeable battery 13, non-contact charging can be carried out through electromagnetic induction simply by placing the main body 2 in the charger 100. The driving circuit 12 includes a central processing unit (CPU) 120 that executes various types of computations and control, a memory 121 that stores programs, various types of configuration values, and so on, a timer 122, a data transmission unit 123, and so on. The data transmission unit 123 carries out wireless communication with a data receiving unit 112 of the display device 110. The display device 110 includes a display 111 for outputting data such as brushing results received by the data receiving unit 112.

Furthermore, a multi-axis (here, three axes, or x, y, and z axes) accelerometer 15, for example, is provided within the main body 2 in order to detect the orientation of the electric toothbrush 1. As shown in FIG. 4, the accelerometer 15 is installed so that the x axis is parallel to a brush surface, the y axis matches the lengthwise direction of the main body 2, and the z axis is perpendicular to the brush surface. In other words, when the main body 2 has been placed in the charger 100, the gravity acceleration vector is parallel to the y axis, when the brush surface is pointed upward, the gravity acceleration vector is parallel to the z axis, and when the main body 2 is placed horizontally and the brush surface is pointed sideways, the gravity acceleration vector is parallel to the x axis. The outputs of the axes of the accelerometer 15 are inputted into the CPU 120, and are used to detect a three-dimensional orientation of the brush.

A piezoelectric resistance-type, an electrostatic capacitance-type, or a thermal detection-type micro electro mechanical systems (MEMS) sensor can be used favorably as the accelerometer 15. MEMS sensors are extremely small and can therefore easily be incorporated into the main body 2. However, the type of the accelerometer 15 is not limited thereto, and an electrokinetic sensor, a strain gauge sensor, a piezoelectric sensor, or the like may be used instead. In addition, although not particularly shown, it is beneficial to provide correction circuits for correcting the balance of sensitivities, temperature characteristics of the sensitivities, temperature drift, and so on of the sensors in the respective axes. Furthermore, a band pass filter (low-pass filter) for removing dynamic acceleration components, noise, and so on may be provided. Further still, noise may be reduced by smoothing the waveforms of the outputs from the accelerometer.

In addition, a load sensor 17 that detects a brush pressure (that is, a load acting on the brush) is provided within the main body 2. Although any type of sensor, such as a strain gauge, a load cell, or a pressure sensor, can be used as the load sensor 17, a MEMS sensor can be used favorably due to its small size and resulting ease of incorporation into the main body 2.

The vibrating member 5 includes a stem portion 20 that is anchored to the main body 2 and a brush component 21 that is mounted to the stem portion 20. Bristles 210 are implanted in the distal end of the brush component 21. The brush component 21 is a consumable item, and is thus configured so as to be removable from the stem portion 20 for replacement.

The brush component 21 of the vibrating member 5 includes a brush portion 3 in which the bristles 210 are disposed and a shank portion 4 located toward the main body 2. Although the present embodiment illustrates a configuration in which the brush component 21 that includes the comparatively long shank portion 4 can be replaced, it should be noted that the configuration may be such that only the brush portion 3, or a brush component that includes the brush portion 3 and a short shank portion, can be replaced. In other words, the configuration may be such that part or all of the shank portion is included as part of the main body.

The stem portion 20 is configured of a resin material. The stem portion 20 is attached to the main body 2 via an elastic member 202 configured of an elastomer. The stem portion 20 is a closed-ended (on the brush-side end) cylindrical member, and has a shaft bearing 203 at a distal end within the cylinder. The distal end of an eccentric shaft 30 that is linked to a rotating shaft 11 of the motor 10 is inserted into the shaft bearing 203 of the stem portion 20. This eccentric shaft 30 has a weight 300 in the vicinity of the shaft bearing 203, and thus the center of gravity of the eccentric shaft 30 is offset from the rotational center thereof. Note that a minute clearance is provided between the distal end of the eccentric shaft 30 and the shaft bearing 203.

The electric toothbrush 1 further includes an electrode-based contact detection unit 50 for detecting contact or proximity. The contact detection unit 50 detects contact with or proximity to a body, or in other words, the cheek mucosa and the tongue, during brushing. Specifically, the contact detection unit 50 includes an electrode portion 52 and a detection portion 54 for detecting an impedance from the electrode portion 52.

The electrode portion 52 includes an electrode 521 disposed on the rear surface of the brush portion 3 (that is, the surface on the opposite side as the brush surface) (also called a "rear surface electrode" hereinafter) and an electrode 522 disposed on the main body 2 (also called a "main body electrode" hereinafter). It is desirable for the main body electrode 522 to be provided on the rear surface of the main body 2 so as to be in continuous contact with the hand of the user during brushing. This is because the principle of action/reaction dictates that it is necessary for a force to be applied to the rear surface of the main body 2. The main body electrode 522 may be extended to as to be aligned with a fingertip of the user. The detection portion 54, meanwhile, may be installed within the driving circuit 12.

The rear surface electrode 521 and the main body electrode 522 may employ a conductive resin material, and may be formed integrally with the members to which they are respectively attached. According to this structure, there is no gap between the members, which makes it possible to ensure water resistance with ease and reduce the buildup of grime. The electrodes may also be formed of metal sheets, or may be formed as thin films through spray coating. The electrodes 521 and 522 may also be provided with recesses and protrusions in order to increase the surface areas thereof. Providing recesses and protrusions also guards against slippage. The recesses and protrusions may be of any shapes.

As shown in FIG. 3, the rear surface electrode 521 is formed integrally with an electrode 61 that is formed within the replaceable brush component 21 and a contact electrode 62 that is exposed at an end of the brush component 21 (that is, the surface that makes contact with the main body 2). The contact electrode 62 functions as a terminal for an electric connection between the main body 2 and the rear surface electrode 521. A contact electrode 63 is provided on an end surface of the main body 2 (on the side that is connected to the brush component 21). The contact electrode 63 is electrically connected to the driving circuit (board) 12 by a lead wire 64. The main body electrode 522 is electrically connected to the driving circuit (board) 12 by a lead wire 65. These electrical components (the electrodes 61, 62, 63 and the lead wires 64 and 65) for electrically connecting the rear surface electrode 521 and the main body electrode 522 shown in FIG. 2 are also included in the electrode portion 52 shown in FIG. 1. The detection portion 54 within the driving circuit 12 is capable of detecting an impedance by detecting a current that flows through the electric circuit configured by the electrode portion 52.

In the case where the configuration is such that only the brush portion 3 or the portion in the vicinity thereof is replaceable as described above, the rear surface electrode may be attached to the shank portion on the main body-side. Doing so makes it possible to simplify the internal configuration of the electrode portion, and also makes it possible to reduce costs when replacing the brush component.

Alternatively, the rear surface electrode may be made removable from the brush component 21. Doing so makes it possible to reuse the rear surface electrode when replacing the brush component 21. Alternatively, both of the exposed electrodes (the rear surface electrode and the main body electrode) may be made replaceable so they can be freely replaced when soiled.

It should be noted that depending on the materials of the components within the main body 2 and the materials of the main body 2 itself, it is possible to configure a closed loop that passes through a human body even without providing the main body electrode 522, and thus the main body electrode 522 need not be included in the electrode portion 52.

Principles of Driving Electric Toothbrush

The CPU 120 supplies driving signals (for example, pulse-width-modulated signals) corresponding to operating modes to the motor 10, thus causing the rotating shaft 11 of the motor 10 to rotate. The eccentric shaft 30 also rotates due to the rotation of the rotating shaft 11, but because the center of gravity of the eccentric shaft 30 is offset, the eccentric shaft 30 moves in gyrations central to the rotational center. Accordingly, the distal end of the eccentric shaft 30 repeatedly collides with the inner wall of the shaft bearing 203, which causes the stem portion 20 and the brush component 21 attached thereto to vibrate (move) at a high rate of speed. In other words, the motor 10 serves as a driving unit that causes the brush to vibrate (move), and the eccentric shaft 30 serves as a motion transmission mechanism (motion conversion mechanism) that converts the output of the motor 10 (that is, rotation) into vibration of the vibrating member 5.

The user can brush his or her teeth by gripping the main body 2 in his or her hand and pressing the bristles 210, which are vibrating at a high rate of speed, against his or her teeth. Note that the CPU 120 monitors the continuous operating time using the timer 122, and automatically stops the vibration of the brush after a predetermined amount of time (for example, two minutes) has passed.

With the electric toothbrush 1 according to the present embodiment, the eccentric shaft 30, which serves as the motion transmission mechanism, is contained within the vibrating member 5, and the weight 300 in particular is disposed in the vicinity of the bristles 210. Therefore, the portion that includes the bristles 210 can be caused to vibrate in an efficient manner. Meanwhile, the vibrating member 5 (the stem portion 20) is attached to the main body 2 via the elastic member 202, and thus the vibration of the vibrating member 5 is not easily transmitted to the main body 2. This makes it possible to reduce vibrations in the main body 2 and in the hand when brushing the teeth, which makes it possible to improve the comfort of use.

Operations of Electric Toothbrush

The manner in which food residue, plaque, and so on adheres to a tooth depends on the type of the tooth (in the maxilla/mandible, whether a molar/incisor, and so on), the area of the tooth (the lingual side/buccal side, the side surface/occlusal surface of the tooth, and so on). Accordingly, effective brushing operations, such as the way in which the brush is applied (the brush angle, brush pressure, and so on), the way the brush is moved, the speed, the brushing time, and so on differ for different areas of the dentition. In light of this, it is desirable to evaluate whether or not proper brushing is being carried out on an area-by-area basis.

Accordingly, the electric toothbrush 1 according to the present embodiment evaluates brushing on an area-by-area basis by accurately estimating a brushing area based on the orientation of the brush as detected by the accelerometer 15 (orientation information) and detection results from the contact detection unit 50. Various items for evaluation are conceivable, but here, three items, or the brushing time, brush angle, and brush pressure, will be described as being evaluated.

Figure 5:
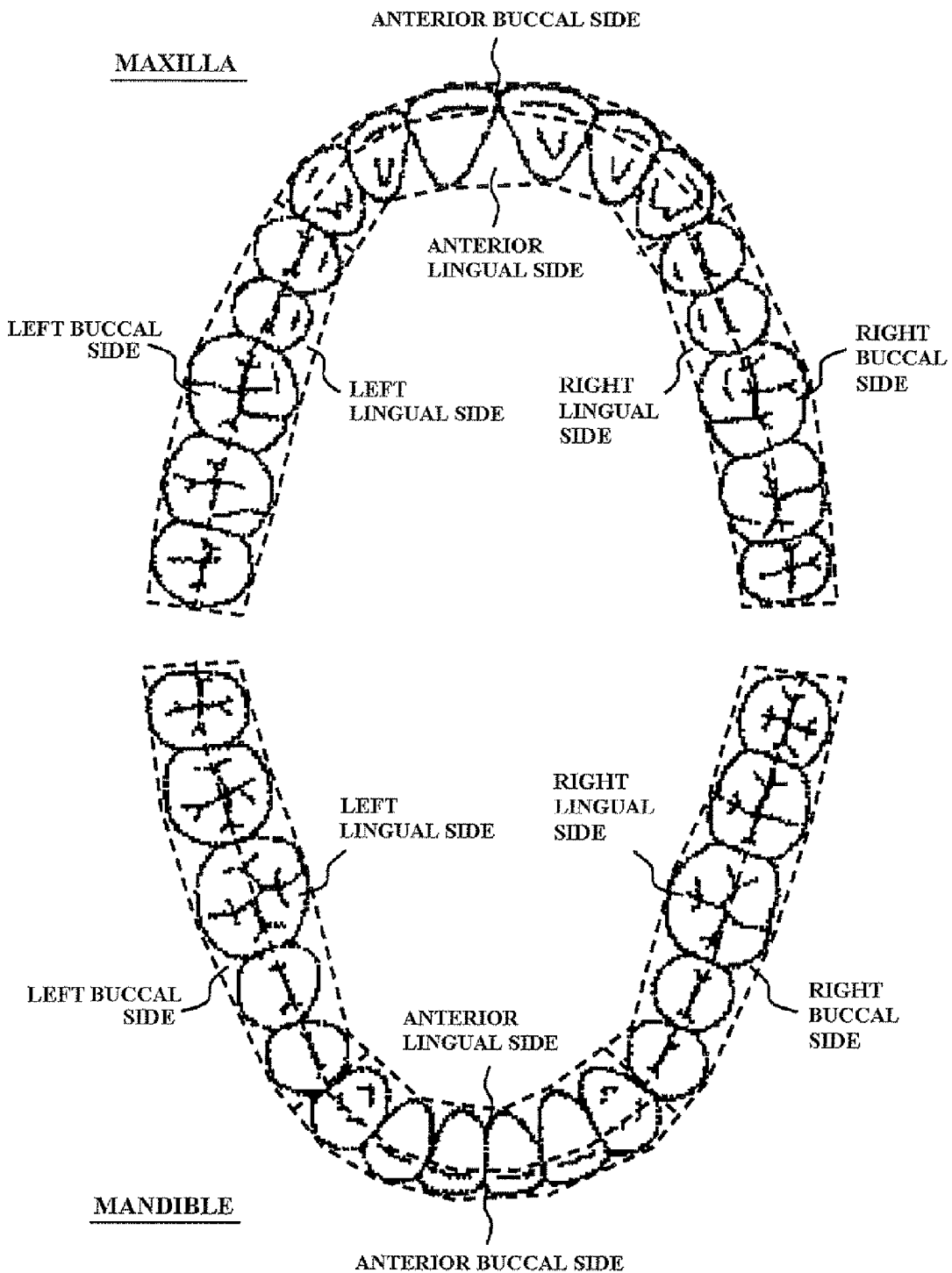
FIG. 5 is a diagram illustrating the segmentation of brushing areas.

In the present embodiment, as shown in FIG. 5, the upper dentition and lower dentition are segmented into 12 areas: a maxillary anterior buccal side; a maxillary anterior lingual side; a maxillary left buccal side; a maxillary left lingual side; a maxillary right buccal side; a maxillary right lingual side; a mandibular anterior buccal side; a mandibular anterior lingual side; a mandibular left buccal side; a mandibular left lingual side; a mandibular right buccal side; and a mandibular right lingual side. However, the segmentation of the dentition is not limited thereto, and broader or narrower segmentation may be carried out instead. For example, the upper and lower left and right occlusal surfaces may be taken into consideration as well.

Note that because the tongue is not present in the maxilla, the maxillary anterior lingual side, maxillary left lingual side, and maxillary right lingual side are given the more precise names of "maxillary anterior palatal side", "maxillary left palatal side", and "maxillary right palatal side", respectively. Likewise, because the cheeks are not present in the forward jaw area, the maxillary anterior buccal side and the mandibular anterior buccal side are given the more precise names of "maxillary anterior labial side" and "mandibular anterior labial side", respectively.

Figure 6:
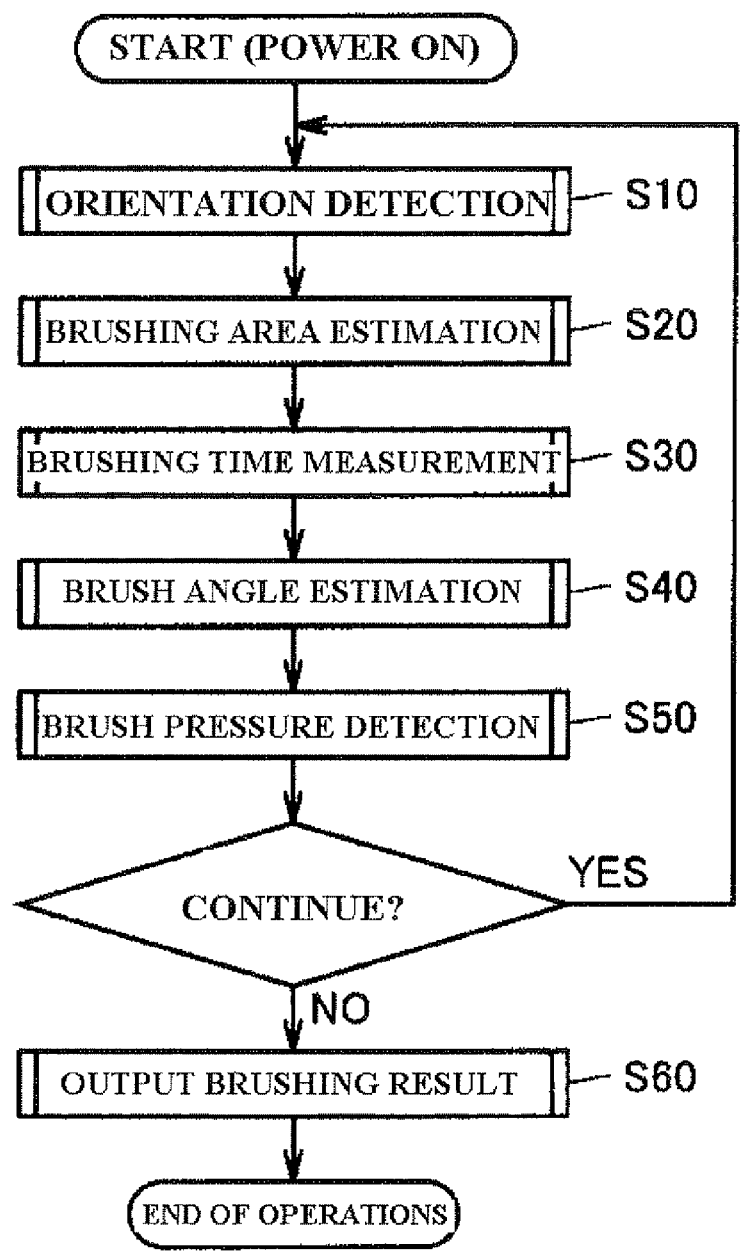
FIG. 6 is a flowchart illustrating a brushing evaluation process according to the first embodiment.
Figure 7:
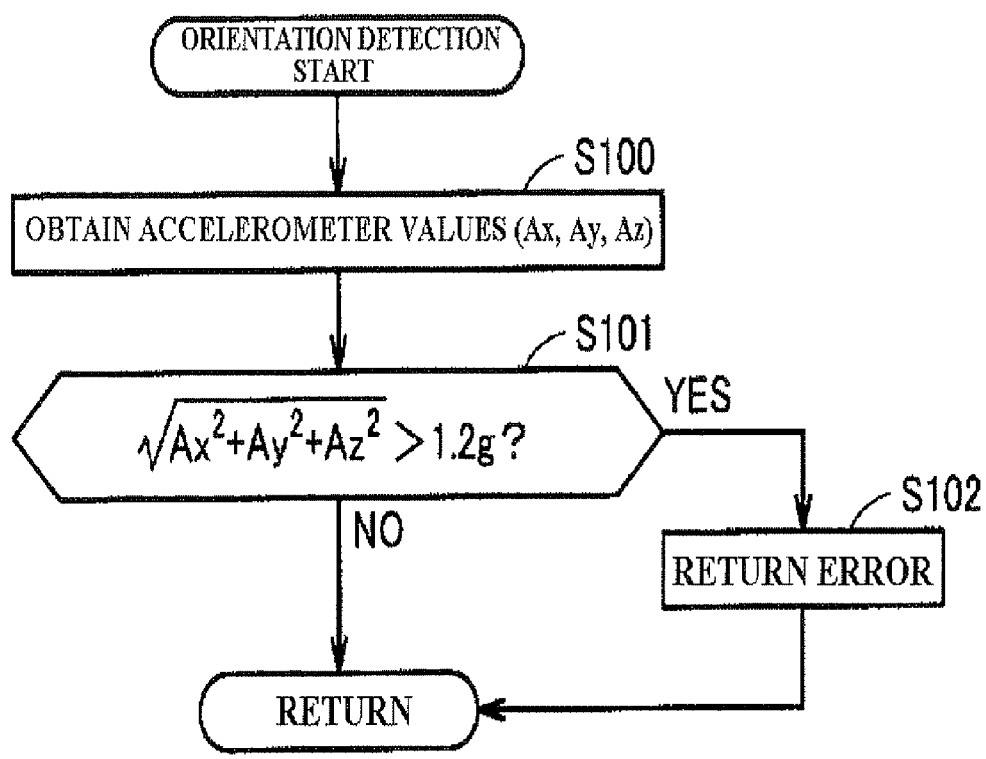
FIG. 7 is a flowchart illustrating an orientation detection process according to the first embodiment.
Figure 8:
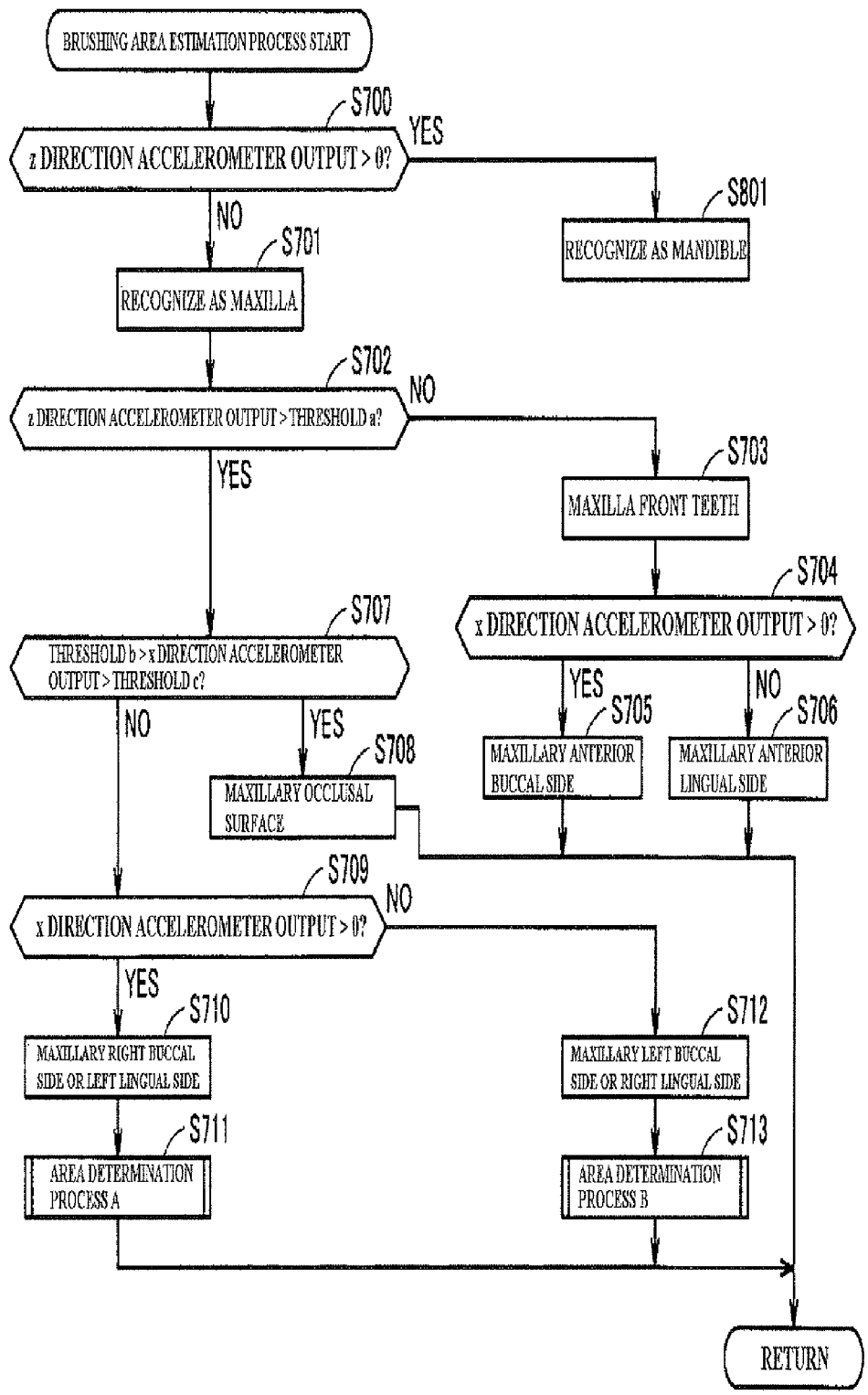
FIG. 8 is a flowchart illustrating a brushing area estimation process (maxilla) according to the first embodiment.
Figure 9:
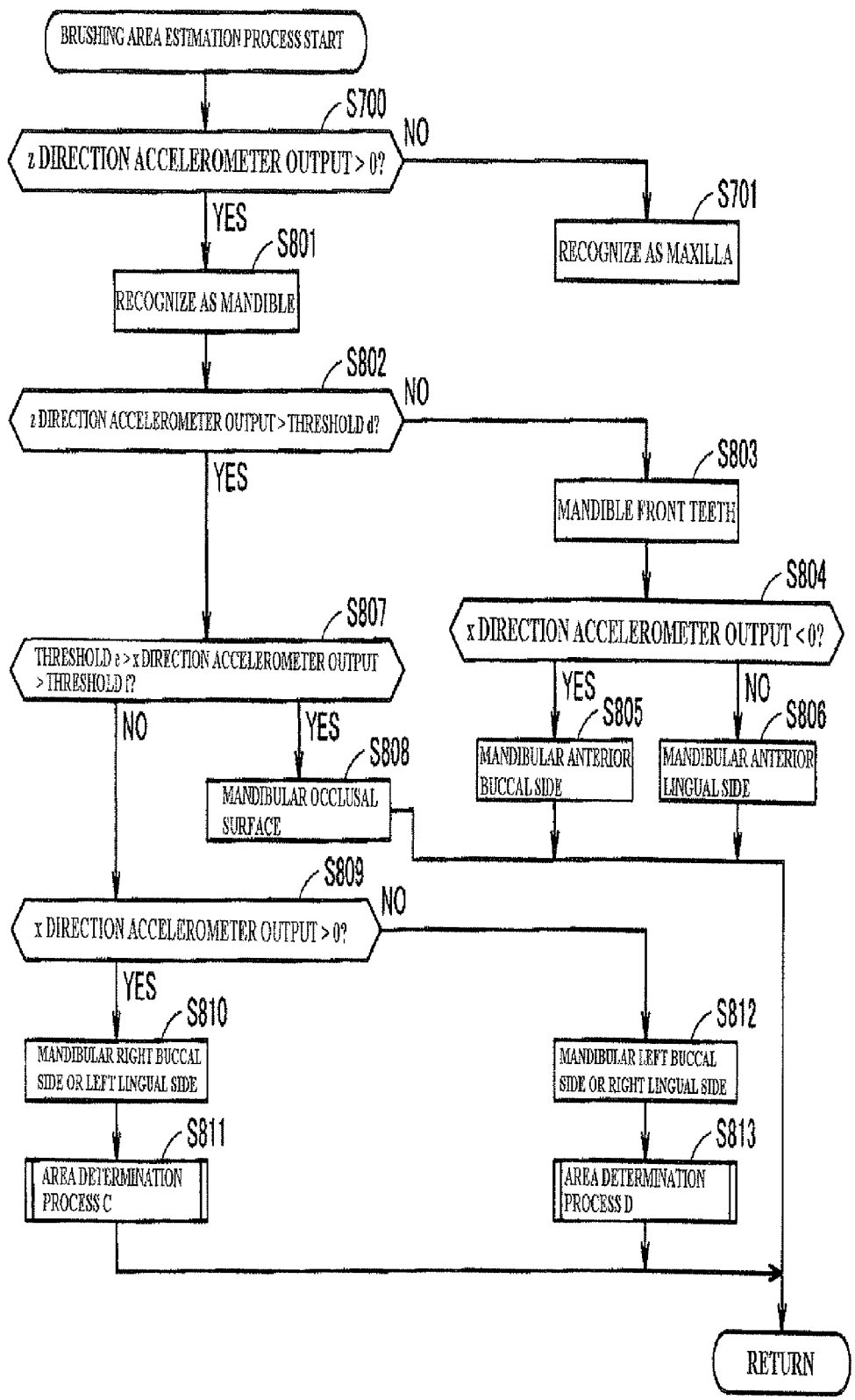
FIG. 9 is a flowchart illustrating a brushing area estimation process (mandible) according to the first embodiment.

A flow of the brushing evaluation will be described in detail with reference to the flowcharts shown in FIGS. 6 through 9. FIG. 6 is a flowchart illustrating a main routine, whereas FIGS. 7 through 9 are flowcharts illustrating various processes in the main routine in detail. Note that unless explicitly mentioned otherwise, the processes described hereinafter are executed by the CPU 120 in accordance with programs stored in the memory 121.

When the electric toothbrush 1 is turned on, the CPU 120 detects the orientation (tilt) of the brush based on the output of the accelerometer 15 (S10). Next, the CPU 120 estimates the brushing area based at least on the orientation detected in S10 (S20). The CPU 120 then measures the brushing time (S30), estimates the brush angle (S40), and detects the brush pressure (S50). These pieces of information are recorded in the memory 121 on an area-by-area basis (see FIG. 18). The processes from S10 to S50 are repeatedly executed every set period of time. When the power is turned off or the continuous operating time has reached a predetermined amount of time (for example, two minutes), the CPU 120 evaluates the brushing result on an area-by-area basis based on the brushing information (the brushing time, brush angle, and brush pressure) recorded in the memory 121, and outputs the evaluation results to the display device 110 (S60). Note that the brushing information in the memory 121 is cleared every time the electric toothbrush 1 is turned on.

Although the brushing results are described as being outputted at the point in time when the brushing has ended in the present embodiment, the brushing results may instead be outputted partway through the brushing while the brushing is being carried out. In other words, the process for outputting the brushing results (S60) may, for example, be carried out between the detection of the brush pressure (S50) and the determination process that follows thereafter.

Hereinafter, the processes in S10 to S60 will be described in detail.

Orientation Detection

FIG. 7 is a flowchart illustrating the orientation detection process (S10).

The CPU 120 obtains outputs Ax, Ay, and Az for the x, y, and z axes, respectively, from the accelerometer 15 (S100). Ax represents an acceleration component in the x direction, Ay represents an acceleration component in the y direction, and Az represents an acceleration component in the z direction. When the electric toothbrush 1 is at rest (that is, when no dynamic acceleration is acting on the accelerometer 15), a combined vector A of Ax, Ay, and Az corresponds to the gravity acceleration. Here, A=(Ax, Ay, Az) is referred to as an orientation vector.

Here, in the case where the magnitude of the orientation vector A=(Ax, Ay, Az) is greater than 1.2 g (where g represents the gravity acceleration) (S101; YES), an error is returned (S102). This is because it is difficult to accurately identify the direction of the gravity acceleration (that is, the three-dimensional orientation of the brush) when a high dynamic acceleration component is present in the accelerometer output. Note that rather than returning an error as in S102, the processes of S100 and S101 may instead be repeated until accelerometer outputs Ax, Ay, and Az from which a combined vector having a magnitude of less than or equal to 1.2 g is obtained. Note also that the threshold value for determining an error is not limited to 1.2 g, and may be a different value instead.

Estimation of Brushing Area

Figure 10:
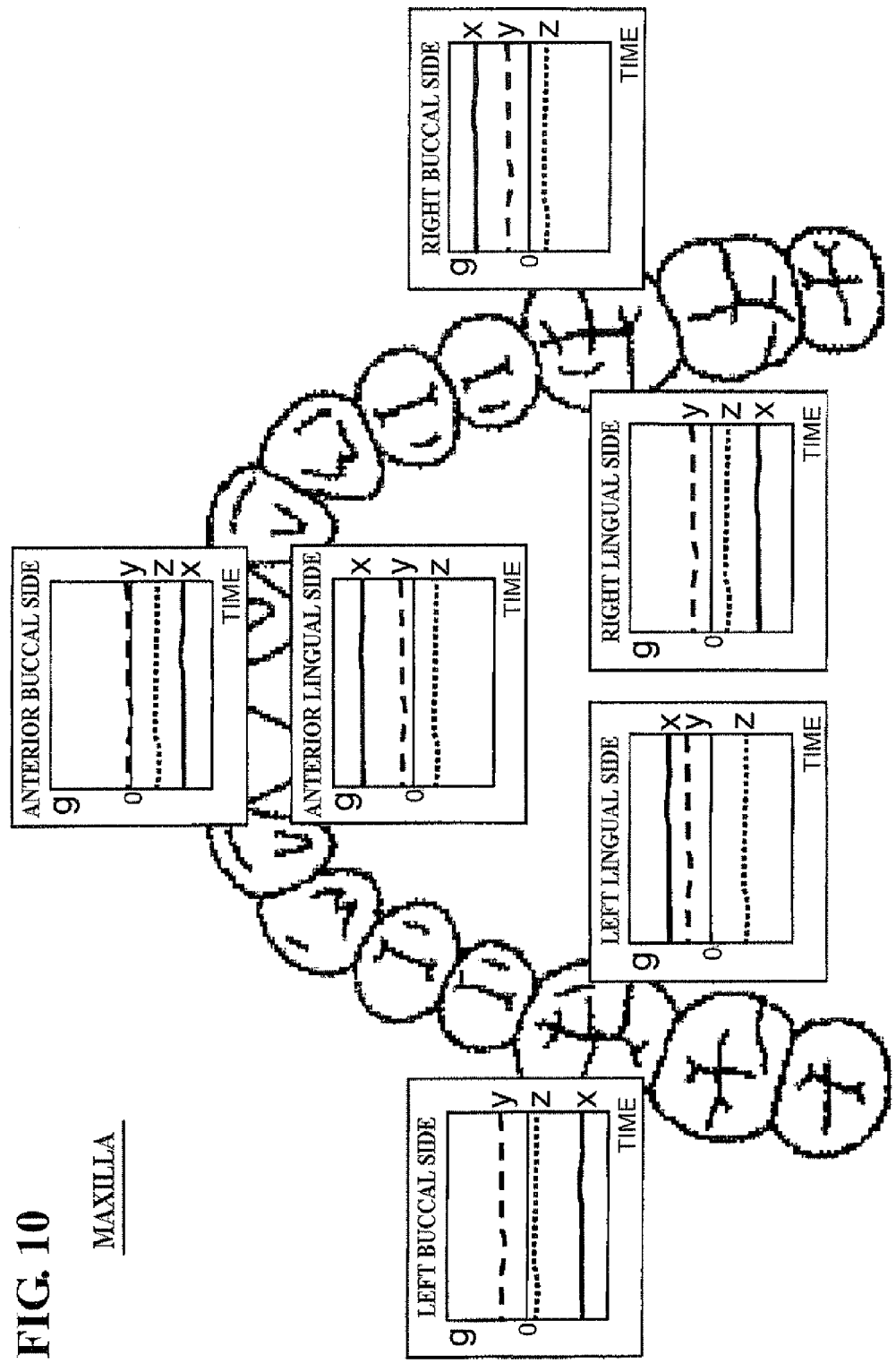
FIG. 10 is a diagram illustrating examples of accelerometer outputs Ax, Ay, and Az for each brushing area in a maxilla.
Figure 11:
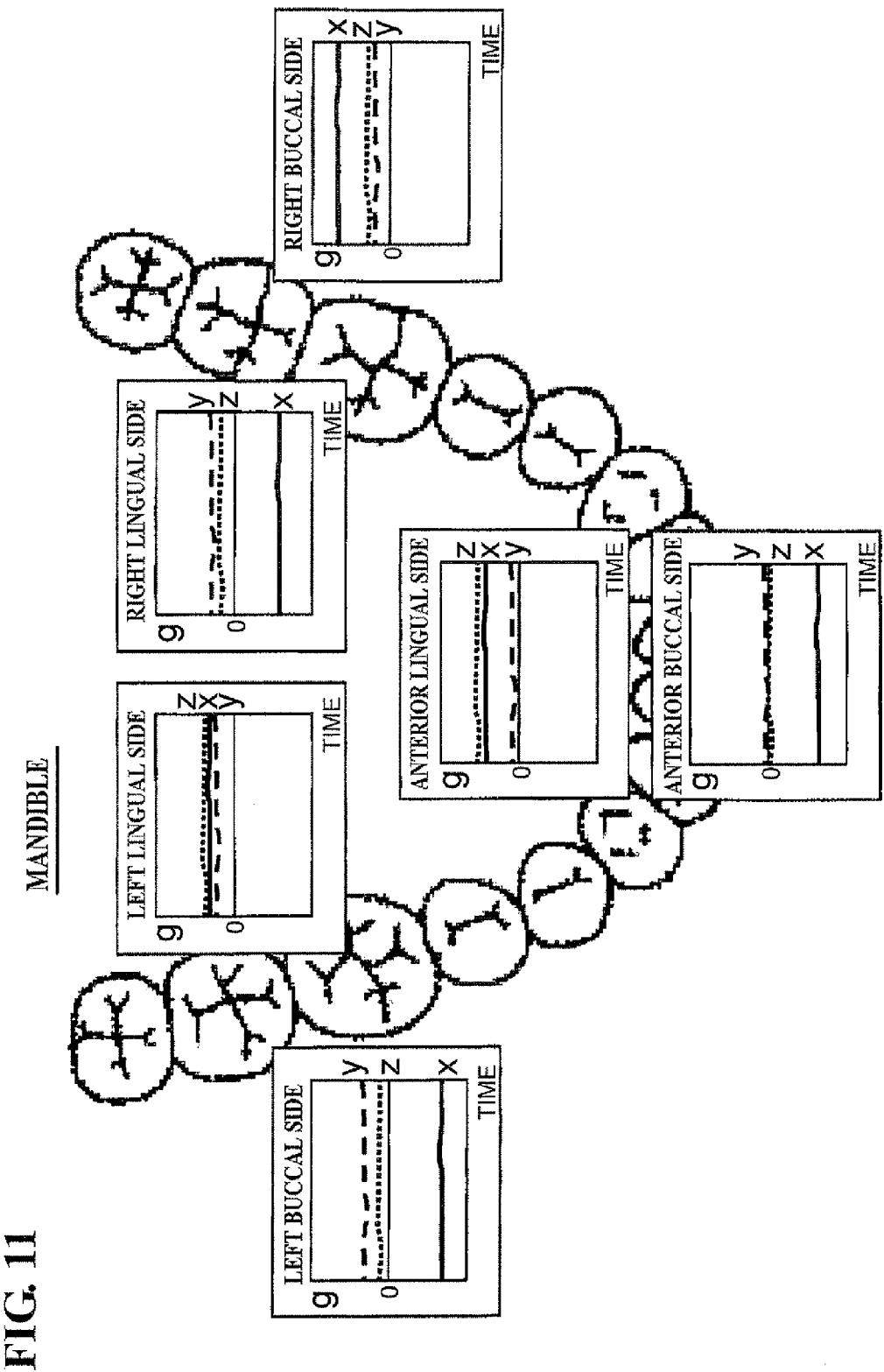
FIG. 11 is a diagram illustrating examples of accelerometer outputs Ax, Ay, and Az for each brushing area in a mandible.

FIGS. 8 and 9 are flowcharts illustrating the brushing area estimation process (S20). Meanwhile, FIGS. 10 and 11 are diagrams illustrating examples of accelerometer outputs Ax, Ay, and Az for the respective brushing areas.

First, the CPU 120 determines whether the brushing area is located at the maxilla or the mandible based on the z direction output Az of the accelerometer (S700). This determination focuses on the fact that when the dentition in the maxilla is being brushed, the brush surface is at least pointed upward, whereas when the dentition in the mandible is being brushed, the brush surface is at least pointed downward. In the case where Az>0, the brushing area is determined to be in the mandible (S801), whereas in the case where Az≦0, the brushing area is determined to be in the maxilla (S701).

(1) Maxilla

The CPU 120 determines whether or not the brushing area corresponds to the front teeth based on the y direction output Ay of the accelerometer (S702). This determination focuses on the fact that although the toothbrush main body 2 is in a comparatively horizontal state when brushing the front teeth, interference with the lips makes it necessary to tilt the toothbrush main body 2 when brushing the molars. The brushing area is determined to correspond to the front teeth of the maxilla in the case where Ay≦a threshold a (S703).

In the case where the brushing area has been determined to correspond to the front teeth of the maxilla, the CPU 120 determines whether the brushing area is on the buccal side or on the lingual side based on the x direction output Ax of the accelerometer (S704). This determination focuses on the fact that the brush faces opposite directions on the buccal side and on the lingual side. The brushing area is determined to correspond to the maxillary anterior buccal side in the case where Ax>0 (S705), whereas the brushing area is determined to correspond to the maxillary anterior lingual side in the case where Ax≦0 (S706).

Meanwhile, in the case where the brushing area has been determined not to correspond to the front teeth of the maxilla in S702, the CPU 120 determines whether the brushing area corresponds to the occlusal surface based on the x direction output Ax of the accelerometer (S707). This determination focuses on the fact that the brush surface is approximately horizontal when brushing the occlusal surface and the Ax output is extremely low as a result. In the case where a threshold b>Ax>a threshold c, it is determined that the brushing area corresponds to an upper-jaw left occlusal surface or an upper-jaw right occlusal surface (S708). Note, however, that in the present embodiment, no particular distinction is made between the upper jaw left occlusal surface and the upper jaw right occlusal surface. This is because there is little necessity to change brushing operations between the left and right sides when brushing the occlusal surface.

In the case where Ax≧the threshold b or Ax≦the threshold c, the CPU 120 determines the direction in which the brush surface is facing based on whether or not Ax is greater than 0 (S709). This determination focuses on the fact that the brush surface faces opposite directions on the buccal side and on the lingual side. In the case where Ax>0, it is determined that the brushing area is the maxillary right buccal side or the maxillary left lingual side (S710), whereas in the case where Ax≦0, it is determined that the brushing area is the maxillary left buccal side or the maxillary right lingual side (S712).

In the case where the brushing area has been determined to be the maxillary right buccal side or the maxillary left lingual side, the area determination process A is executed (S710). In the case where the brushing area has been determined to be the maxillary left buccal side or the maxillary right lingual side, the area determination process B is executed (S711). The area determination processes A and B will be described later.

(2) Mandible

The CPU 120 determines whether or not the brushing area corresponds to the front teeth based on the y direction output Ay of the accelerometer (S802). This determination focuses on the fact that although the toothbrush main body 2 is in a comparatively horizontal state when brushing the front teeth, interference with the lips makes it necessary to tilt the toothbrush main body 2 when brushing the molars. The brushing area is determined to correspond to the front teeth of the mandible in the case where Ay≦a threshold d (S803).

In the case where the brushing area has been determined to correspond to the front teeth of the mandible, the CPU 120 determines whether the brushing area is on the buccal side or on the lingual side based on the x direction output Ax of the accelerometer (S804). This determination focuses on the fact that the brush faces opposite directions on the buccal side and on the lingual side. In the case where Ax<0, the brushing area is determined to correspond to the mandibular anterior buccal side (S805), whereas in the case where Ax≧0, the brushing area is determined to correspond to the mandibular anterior lingual side (S806).

Meanwhile, in the case where the brushing area has been determined not to correspond to the front teeth of the mandible in S802, the CPU 120 determines whether the brushing area corresponds to the occlusal surface based on the x direction output Ax of the accelerometer (S807). This determination focuses on the fact that the brush surface is approximately horizontal when brushing the occlusal surface and the Ax output is extremely low as a result. In the case where a threshold e>Ax>a threshold f, it is determined that the brushing area corresponds to a lower-jaw left occlusal surface or a lower-jaw right occlusal surface (S808). Note, however, that in the present embodiment, no particular distinction is made between the lower-jaw left occlusal surface and the lower-jaw right occlusal surface. This is because there is little necessity to change brushing operations between the left and right sides when brushing the occlusal surface.

In the case where Ax≧the threshold e or Ax≦the threshold f, the CPU 120 determines the direction in which the brush surface is facing based on whether or not Ax is greater than 0 (S809). This determination focuses on the fact that the brush surface faces opposite directions on the buccal side and on the lingual side. In the case where Ax>0, the brushing area is determined to correspond to the mandibular right buccal side or the mandibular left lingual side (S810), whereas in the case where Ax≦0, the brushing area is determined to correspond to the mandibular left buccal side or the mandibular right lingual side (S812).

In the case where the brushing area has been determined to be the mandibular right buccal side or the mandibular left lingual side, the area determination process C is executed (S811). In the case where the brushing area has been determined to be the mandibular left buccal side or the mandibular right lingual side, the area determination process D is executed (S813).

The stated determination algorithm is merely an example, and any determination algorithm may be employed as long as it is capable of detecting a brushing area from the outputs Ax, Ay, and Az of the accelerometer 15. For example, rather than using the values of Ax, Ay, and Az directly as the variables for the determination, two-dimensional variables obtained by combining Ax, Ay, and Az as appropriate may be used in the determination instead. The two-dimensional variables can be set as desired, such as Ay/Az, Ax·Ax+Ay·Ay, Az−Ax, and so on. Alternatively, the brushing area may be determined after converting the acceleration information Ax, Ay, and Az from the respective axes into angle information (orientation angles) α, β, and γ. For example, the angle of the x axis relative to the gravity acceleration direction may be defined as a roll angle α, the angle of the y axis relative to the gravity acceleration direction may be defined as a pitch angle β, and the angle of the z axis relative to the gravity acceleration direction may be defined as a yaw angle γ. The thresholds used in the determinations can be set based on the results of clinical experiments or the like.

Area Determination Processes

Processes for determining whether the brushing area corresponds, to the buccal side or to the lingual side in the case where the brushing area has been determined to correspond to the right buccal-side or left-lingual side dentition surface, or to the left buccal-side or right-lingual side dentition surface, will be described. In other words, area determination processes for determining whether the brushing area corresponds to the buccal side or the lingual side (the palatal side) in the case where the brushing area has been determined to correspond to the maxillary right buccal side or maxillary left lingual side, to the maxillary left buccal side or maxillary right lingual side, to the mandibular right buccal side or mandibular left lingual side, or to the mandibular left buccal side or mandibular right lingual side, will be described.

Figure 12:
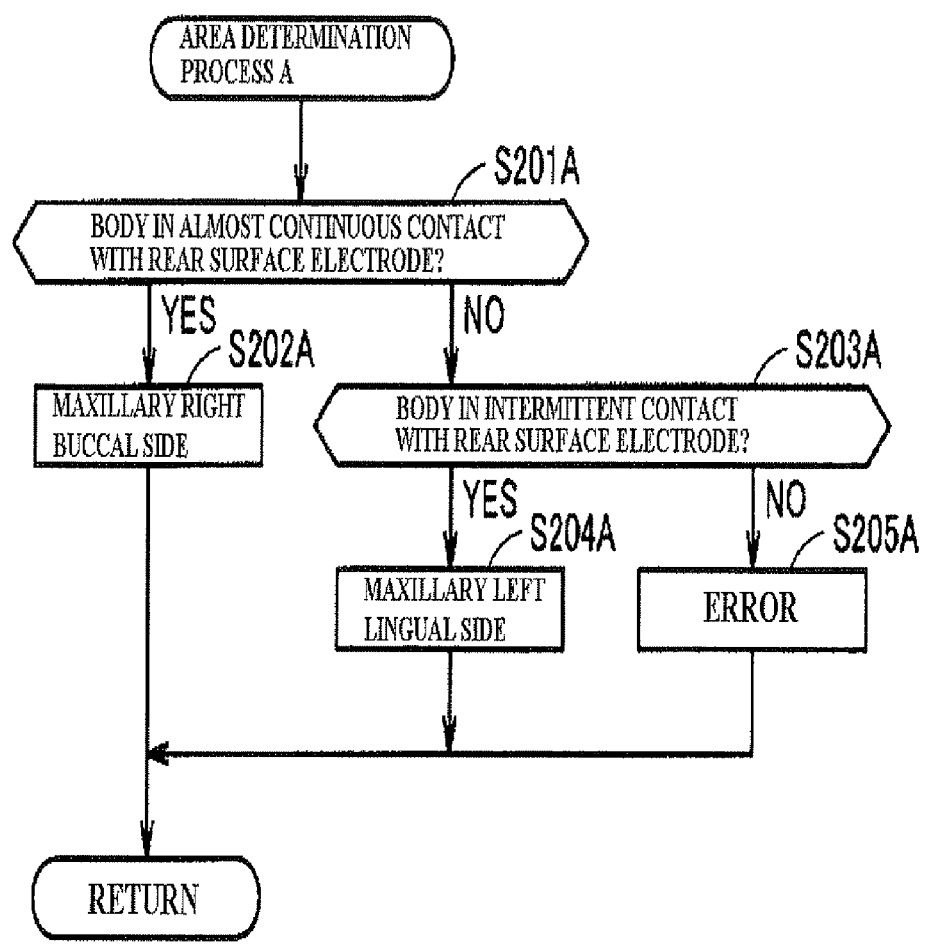
FIG. 12 is a flowchart illustrating an area determination process A included in the brushing area estimation process shown in FIG. 8.

FIG. 12 is a flowchart illustrating the area determination process A.

The CPU 120 determines whether or not the electrode 521 disposed on the rear surface of the brush portion 3 (that is, the rear surface electrode) is in almost continuous contact with the body (S201A). For example, the CPU 120 determines whether or not the percentage of contact time within a set amount of time is greater than or equal to 80%. Whether or not contact is made with the body can be determined based on an impedance value detected by the detection portion 54 or based on a change therein.

FIGS. 13A and 13B are diagrams schematically illustrating a circuit passing through a body in a state in which the rear surface electrode 521 is in contact with the body and a state in which the rear surface electrode 521 is not in contact with the body.

As shown in FIG. 13A, an air section is present when the rear surface electrode 521 is not in contact with the body, and thus the impedance value is higher than when contact is being made. On the other hand, as shown in FIG. 13B, when the rear surface electrode 521 is in contact with the body, a closed-loop circuit that passes through the rear surface electrode 521 is configured, and thus the impedance value is lower than when contact is not being made.

Accordingly, whether or not contact is being made can be determined by, for example, detecting whether or not the impedance value is greater than or equal to a predetermined threshold. The impedance threshold is determined in advance through experimentation.

In the case where it has been determined that the rear surface electrode 521 is in almost constant contact with the body (YES in S201A), it is determined that the brushing area corresponds to the maxillary right buccal side (S202A). This is because the rear surface of the brush portion 3 in the electric toothbrush 1 is in almost constant contact with the inner cheek when brushing on the buccal side.

On the other hand, in the case where it has been determined that the rear surface electrode 521 is not in almost constant contact with the body (NO in S201A), it is furthermore determined whether or not the rear surface electrode 521 is in intermittent contact with the body (S203A). For example, the CPU 120 determines whether or not the percentage of contact time within a set amount of time is greater than or equal to 30% and less than 80%. In the case where it has been determined that the rear surface electrode 521 is in intermittent contact with the body (YES in S203A), it is determined that the brushing area corresponds to the maxillary left lingual side (S204A). This is because the rear surface of the brush portion 3 in the electric toothbrush I makes contact with the tongue intermittently when brushing the lingual side (the palatal side).

In the case where it has been determined that the rear surface electrode 521 is not making intermittent contact with the body (NO in S203A), an error is determined to have occurred (S205A).

Figure 14:
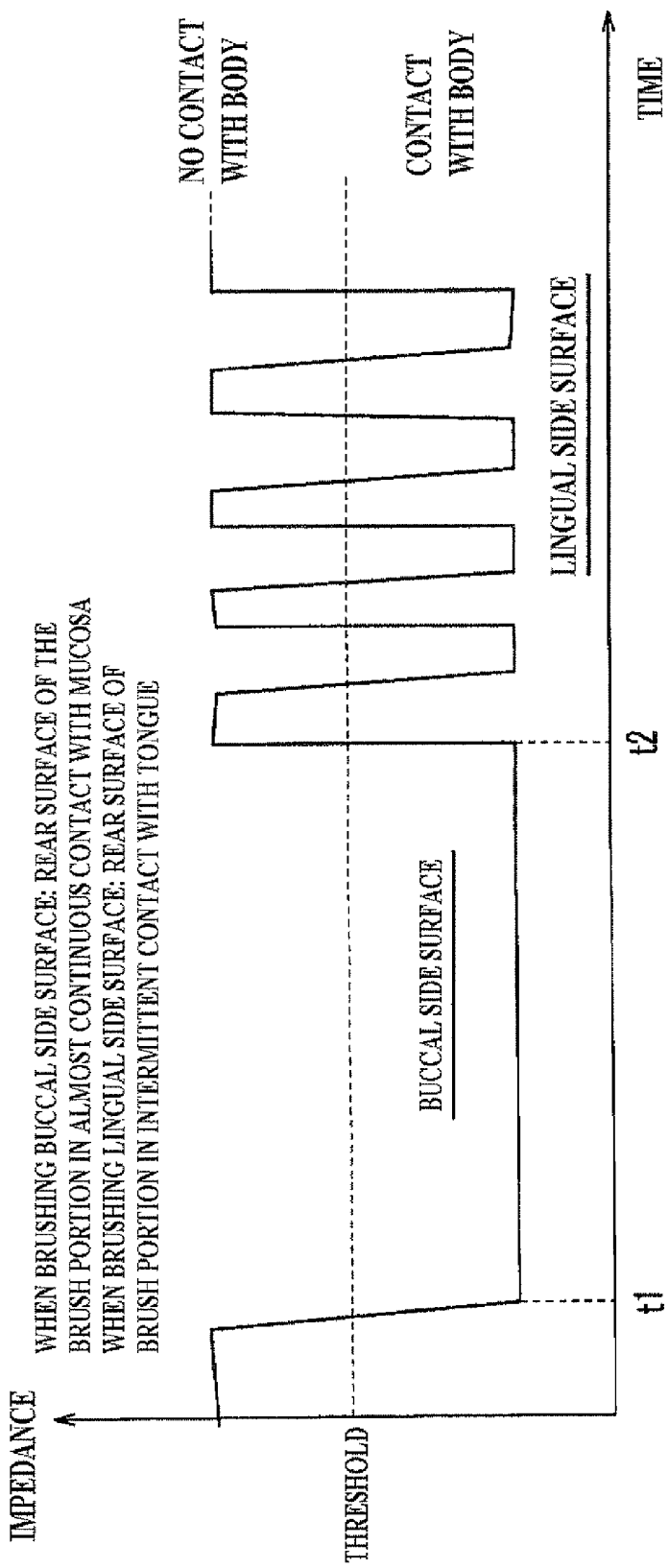
FIG. 14 is a diagram illustrating a specific example of a method for determining between a buccal side and a lingual side according to the first embodiment.

A specific example of the method for determining between the buccal side/lingual side according to the present embodiment is illustrated in FIG. 14. Note that in order to obtain impedance levels such as those shown in FIG. 14, for example, a pair of electrodes for current application and a pair of electrodes for voltage detection, as are employed in body fat meters, may be provided on the rear surface of the brush portion 3.

As shown in FIG. 14, the impedance value is constantly less than the threshold from time t1 to t2, and thus the brushing area is determined to be the buccal-side surface. However, from time t2, the impedance value intermittently rises above the threshold, and thus the brushing area is determined to be the lingual-side surface.

Figure 15:
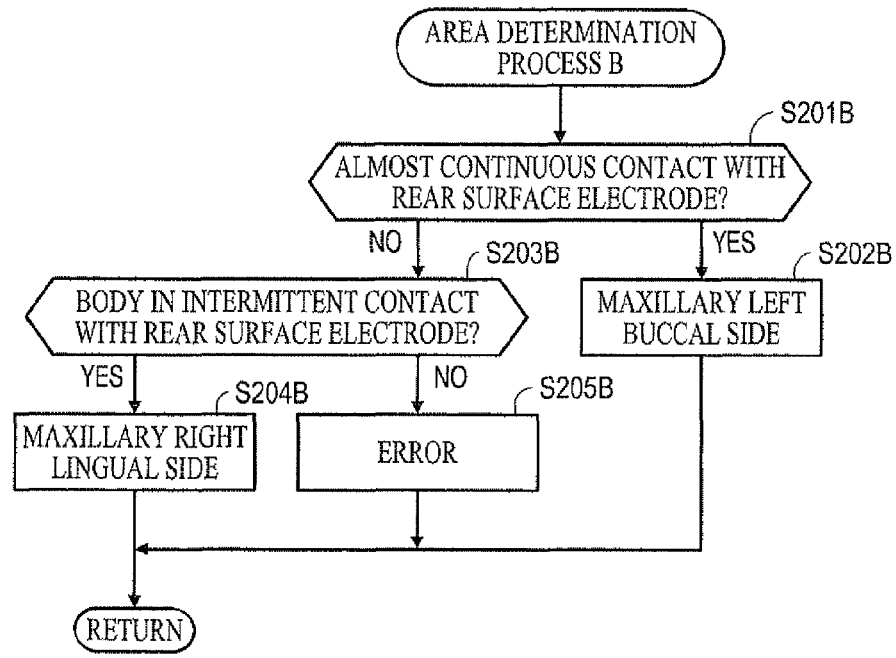
FIG. 15 is a flowchart illustrating an area determination process 13 included in the brushing area estimation process shown in FIG. 8.
Figure 16:
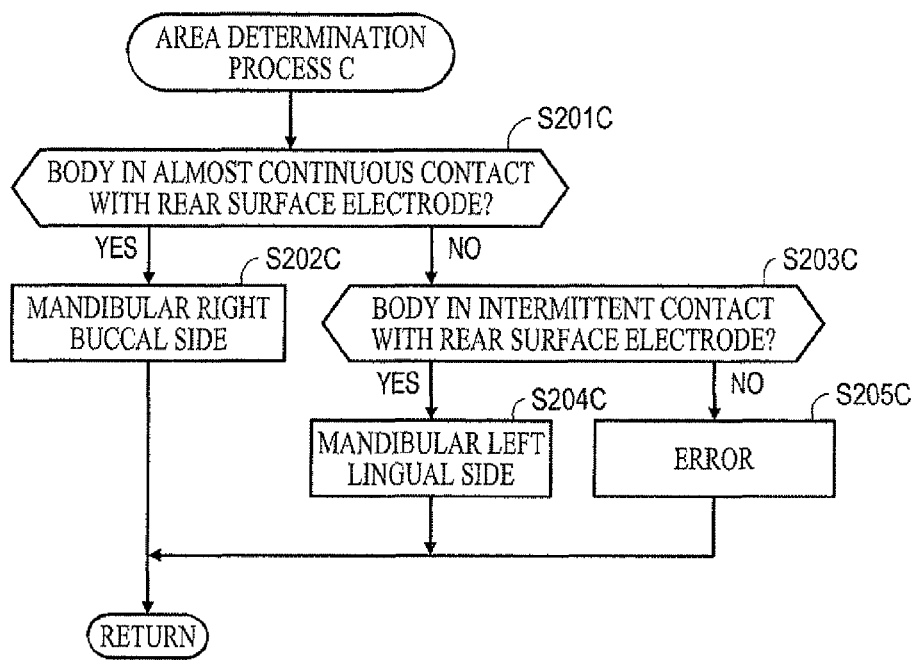
FIG. 16 is a flowchart illustrating an area determination process C included in the brushing area estimation process shown in FIG. 9.
Figure 17:
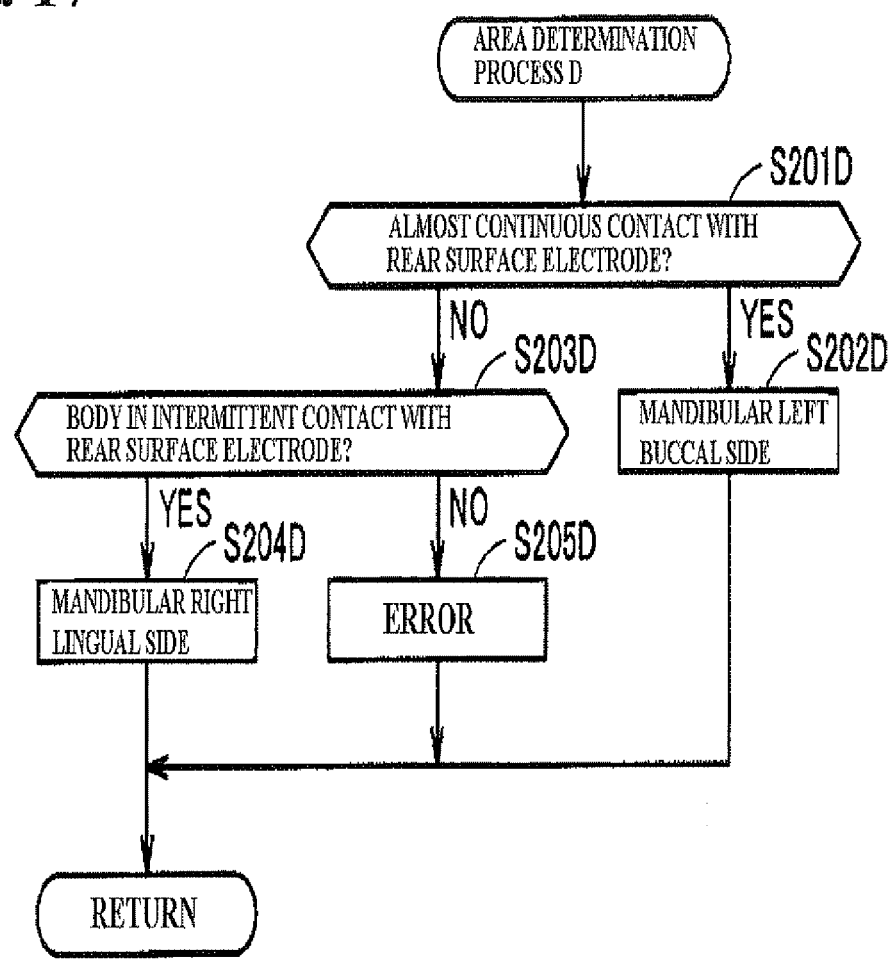
FIG. 17 is a flowchart illustrating an area determination process D included in the brushing area estimation process shown in FIG. 9.

FIGS. 15 through 17 are flowcharts illustrating the area determination processes B, C, and D, respectively. The processes illustrated in these flowcharts are basically the same as the area determination process A shown in FIG. 12. The differences lie in that the maxillary right buccal side (S202A) and the maxillary left lingual side (S204A) shown in FIG. 12 differ based on the general area determination results prior to moving to the area determination processes. Specifically, in the area determination process B shown in FIG. 15, the brushing areas are determined to be the maxillary left buccal side (S202B) and the maxillary right lingual side (S204B), respectively, instead of the maxillary right buccal side (S202A) and the maxillary left lingual side (S204A) in the area determination process A shown in FIG. 12. With the area determination process C shown in FIG. 16, the brushing areas are determined to be the mandibular right buccal side (S202C) and the mandibular left lingual side (S204C), respectively, instead of the maxillary right buccal side (S202A) and the maxillary left lingual side (S204A) in the area determination process A shown in FIG. 12. With the area determination process D shown in FIG. 17, the brushing areas are determined to be the mandibular left buccal side (S202D) and the mandibular right lingual side (S204D), respectively, instead of the maxillary right buccal side (S202A) and the maxillary left lingual side (S204A) in the area determination process A shown in FIG. 12.

Through the stated processes, the current brushing area is determined to be one of the maxillary anterior buccal side (S705), the maxillary anterior lingual side (S706), the maxillary occlusal surface (S708), the maxillary right buccal side (S202A), the maxillary left lingual side (S204A), the maxillary left buccal side (S202B) or maxillary right lingual side (S204B), the mandibular anterior buccal side (S805), the mandibular anterior lingual side (S806), the mandibular occlusal surface (S808), the mandibular right buccal side (S202C), the mandibular left lingual side (S204C), the mandibular left buccal side (S202D), and the mandibular right lingual side (S204D).

Note that in the present embodiment, the determination between the buccal side and the lingual side is carried out by detecting impedance values in a set amount of time, and thus the result of the determination between the buccal side and the lingual side may be first obtained after performing multiple cycles of the brushing area estimation process (S20 in FIG. 6).

In addition, because an evaluation result is not outputted for the occlusal surface in the present embodiment, the area determination for the occlusal surface may be omitted.

Brushing Time Measurement

FIG. 18 illustrates an example of brushing information recorded in the memory 121. FIG. 18 shows an example of a state in which the mandibular left buccal side is being brushed. Here, it is assumed that the maxillary anterior buccal side has been brushed for 7.5 seconds prior to the mandibular left buccal side, and that the maxillary left buccal side is being brushed for 12.2 seconds. Note that a "-" indicates that no data is recorded, or in other words, that the area in question has not yet been brushed.

In S30 of FIG. 6, the CPU 120 counts up the brushing time for the brushing area estimated in S20 (the mandibular left buccal side, in the example shown in FIG. 18). For example, if the processes from S10 to S50 in FIG. 6 are executed once every 0.1 seconds, the brushing time for the mandibular left buccal side is counted up by 0.1, and is thus 2.1 seconds.

Note that the cumulative brushing time is recorded in the brushing information. In other words, in the case where, for example, the brushing area has moved to the maxillary left buccal, side for a second time, the brushing time stored in the memory is not reset; instead, the brushing time is added to the value stored in the memory, i.e., a brushing time of 12.2 seconds.

Brush Angle Estimation

In S40 of FIG. 6, the CPU 120 estimates the brush angle based on the orientation detected in S10 (that is, the output of the accelerometer 15), and updates the value of the brush angle for the current brushing area (the mandibular left buccal side, in the example shown in FIG. 18). At this time, it is preferable for the CPU 120 to calculate and record an average value for the brush angle from the value of the brush angle stored in the memory and the value estimated as described here.

The brush angle is the angle at which the brush makes contact with the tooth axis (that is, the axis that spans from the crown to the root of the tooth). FIG. 19A illustrates a state in which the brush angle is 15°, FIG. 19B illustrates a state in which the brush angle is 45°, and FIG. 19C illustrates a state in which the brush angle is 90°. In order to effectively remove food residue, plaque, and so on from the periodontal pockets, from between the teeth, and so on, it is preferable to move the brush so that the tips of the bristles enter into the periodontal pockets, between the teeth, and so on. Therefore, it is preferable for the brush angle to be within a range from 35° to 55°.

Figure 20:
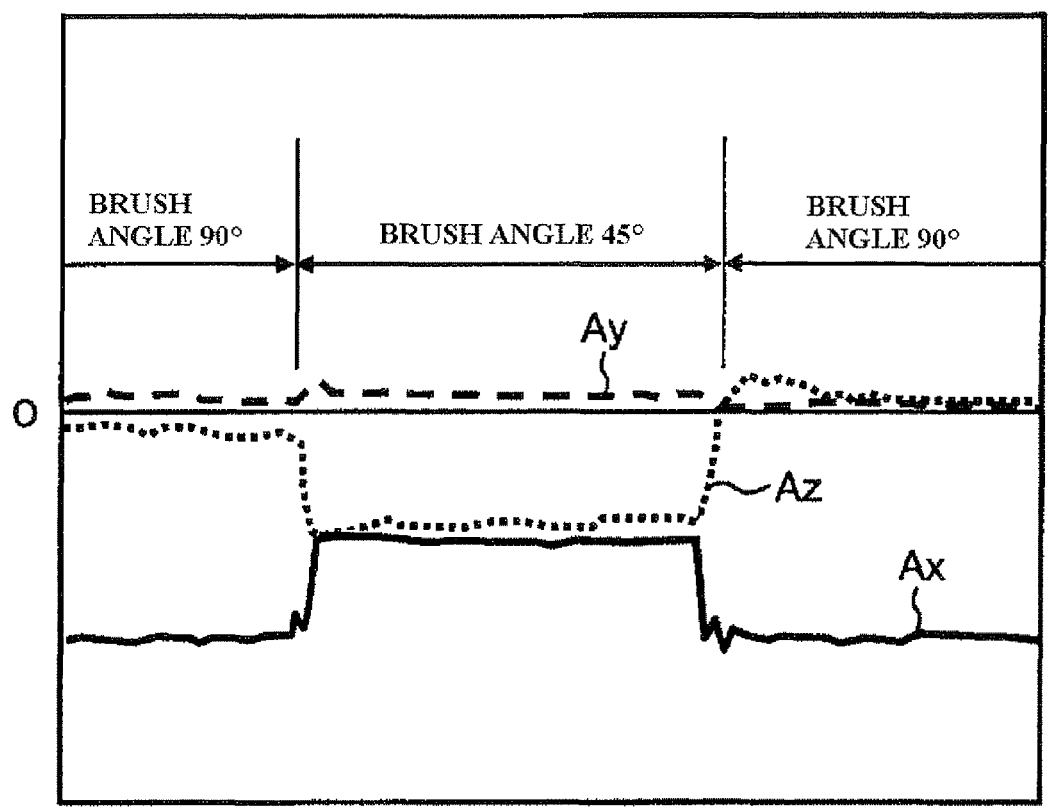
FIG. 20 is a diagram illustrating waveform changes in sensor outputs resulting from changes in the brush angle.

The brush angle can be estimated, for example, from the z direction acceleration component Az. This is because as shown in FIG. 20, the value of Az changes significantly in accordance with the brush angle, with Az being almost 0 in the case where the brush angle is approximately 90° and increasing as the brush angle decreases. Note that the x direction acceleration component Ax also changes in accordance with the brush angle, and thus it is also favorable to estimate the brush angle based on Ax instead of Az, estimate the brush angle based on both Ax and Az (that is, based on the direction of the combined vector of Ax and Az), and so on. The length for which the brush angle continues may also be calculated, or the brush angle may be estimated in a general manner, such as "less than 35°", "between 35° and 55°", "greater than or equal to 55°", and so on.

Brush Pressure Detection

In S50 of FIG. 6, the CPU 120 calculates the brush pressure based on the output of the load sensor 17, and updates the value of the brush pressure for the current brushing area (the mandibular left buccal side, in the example shown in FIG. 18). At this time, it is preferable for the CPU 120 to calculate and record an average value for the brush pressure from the value of the brush pressure stored in the memory and the value detected as described here.

Too low a brush pressure reduces the effectiveness of plaque removal, and conversely, too high a brush pressure may result in problems such as a reduction in the lifespan of the brush, an increase in the burden on the gums, and so on. Because electric toothbrushes require a lower brush pressure than normal toothbrushes, it is said that almost all people who have begun using electric toothbrushes tend to apply too much brush pressure. The optimal value for the brush pressure is approximately 100 g.

Evaluation/Output of Brushing Results

Based on the brushing information recorded in the memory 121, the CPU 120 evaluates the brushing results on an area-by-area basis, and outputs the evaluation results to the display device 110 (the display 111).

Figure 21:
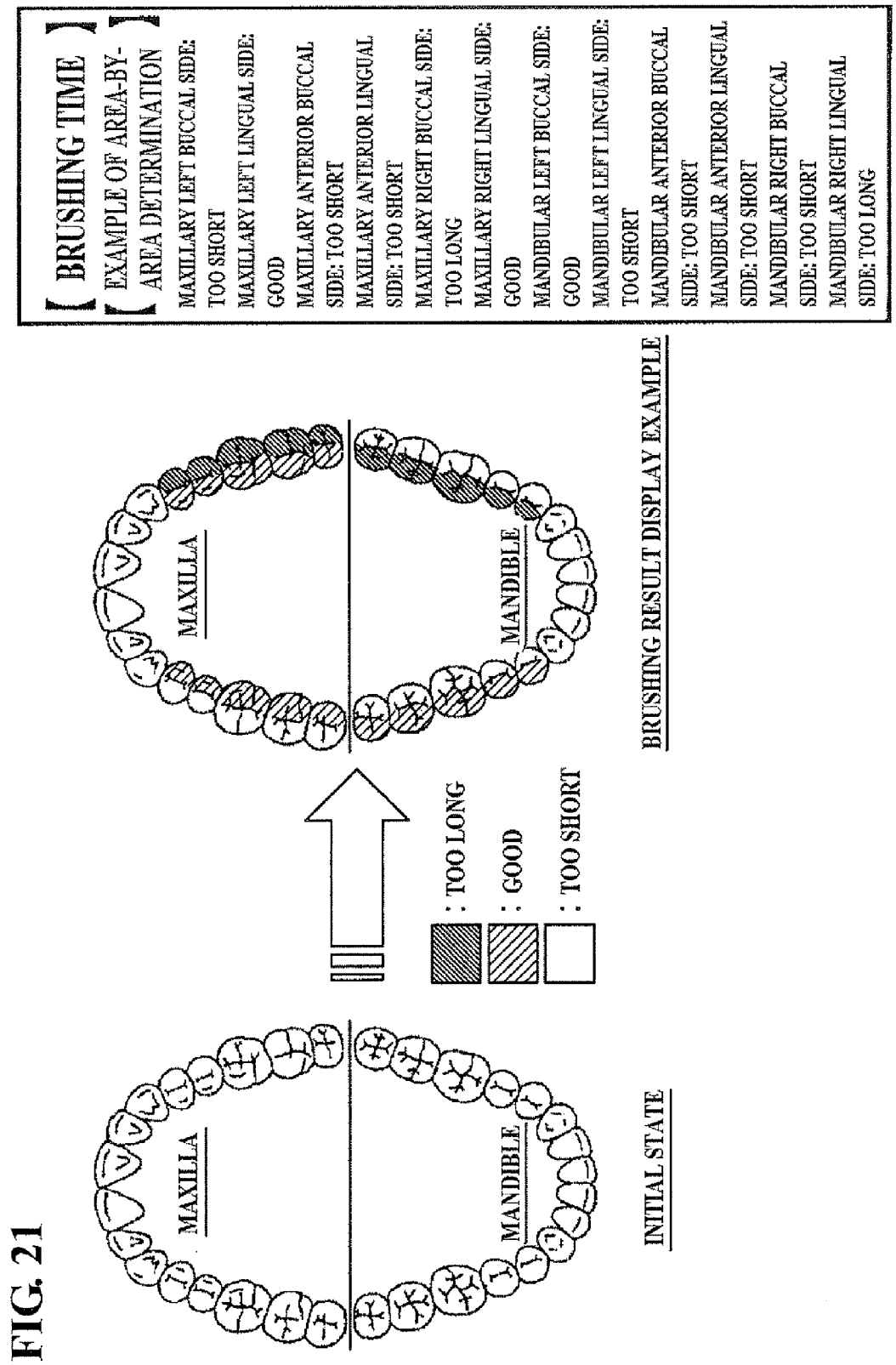
FIG. 21 is a diagram illustrating an example of the output of a brushing time serving as a brushing result.

FIG. 21 is an example of the output of an evaluation result for the brushing time. The CPU 120 loads the brushing time for each area from the memory 121, and evaluates, for example, less than 7 seconds as "too short", 7 to 15 seconds as "good", and more than 15 seconds as "too long". These evaluation results are then sent to the display device 110. The dentition is displayed in the display 111 of the display device 110, and the areas within the dentition are indicated by colors that correspond to evaluation results ("too short" by white, "good" by yellow, "too long" by red, and so on). By viewing this display, the user can intuitively grasp which area of the dentition has not been brushed enough (or has been brushed too much).

Figure 22:
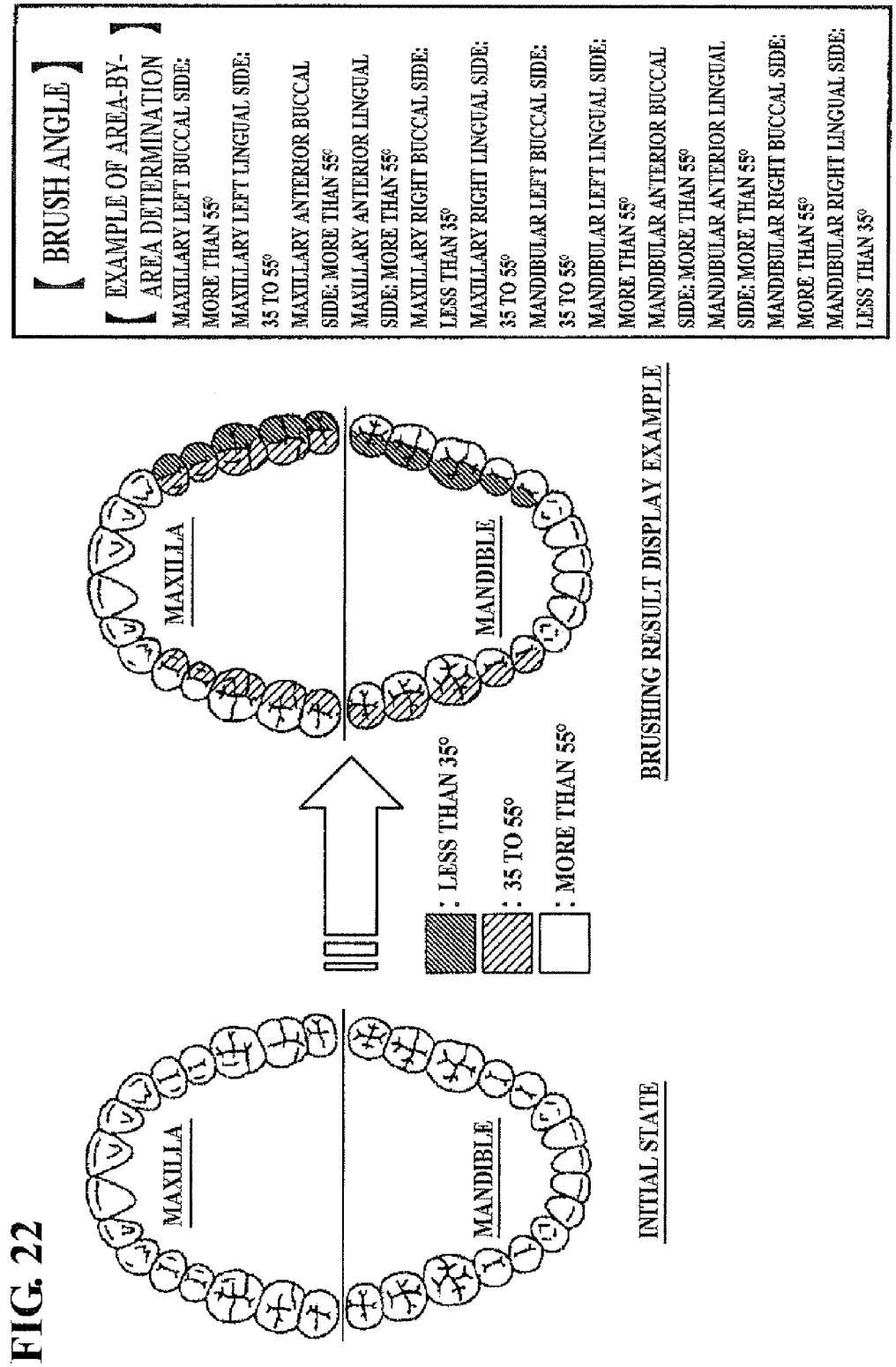
FIG. 22 is a diagram illustrating an example of the output of a brush angle serving as a brushing result.

FIG. 22 is an example of the output of an evaluation result for the brush angle. For example, the brush angle is evaluated in three stages, or "less than 35°", "35° to 55°", and "greater than 55°", and the various areas in the dentition are indicated by colors that correspond to the evaluation results. Because the effectiveness of plaque removal is lower when brushing is carried out at an improper brush angle than when brushing is carried out at a proper brush angle, there is the possibility that the desired brushing results will not be obtained, the brushing will take more time, and so on. As shown in FIG. 22, if brush angle evaluations are outputted for each area, the user can be made aware of how to brush using the proper brush angle.

Figure 23:
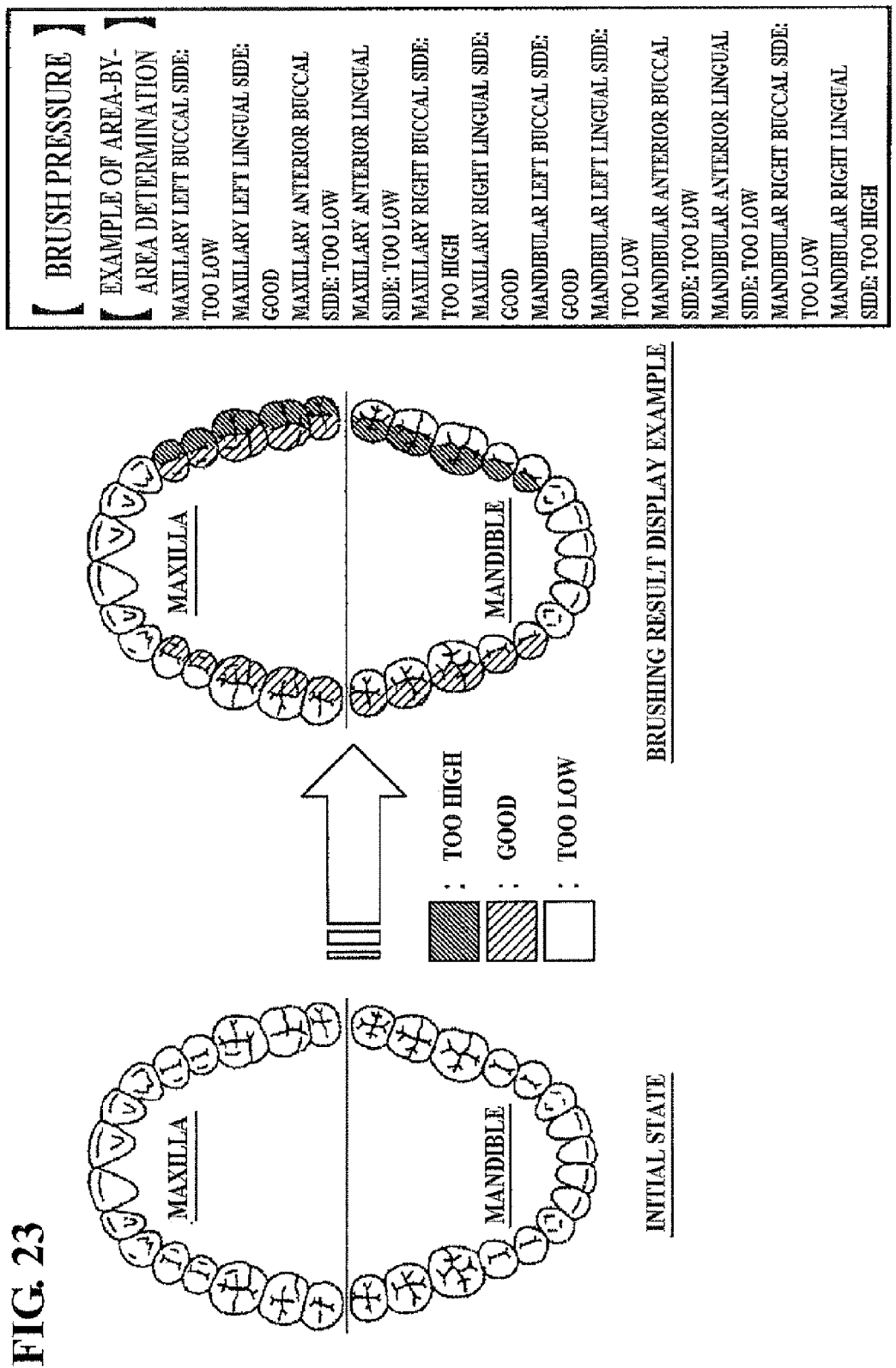
FIG. 23 is a diagram illustrating an example of the output of a brush pressure serving as a brushing result.

FIG. 23 is an example of the output of an evaluation result for the brush pressure. For example, the brush pressure is evaluated as "too low" for less than 80 g, "good" for 80 g to 150 g, and "too high" for more than 150 g, and the various areas in the dentition are indicated by colors that correspond to the evaluation results. If the brush pressure is improper as described above, there is the possibility that problems such as a drop in the effectiveness of plaque removal, a decrease in the lifespan of the brush, an increase in the burden on the gums, and so on will occur. However, it is difficult for the user to understand how much pressure corresponds to the optimum brush pressure. With respect to this point, if brush pressure evaluations are outputted for each area as shown in FIG. 23, the user can be informed of the proper brush pressure, and can thus be made aware of how to brush with the proper brush pressure.

Figure 24:
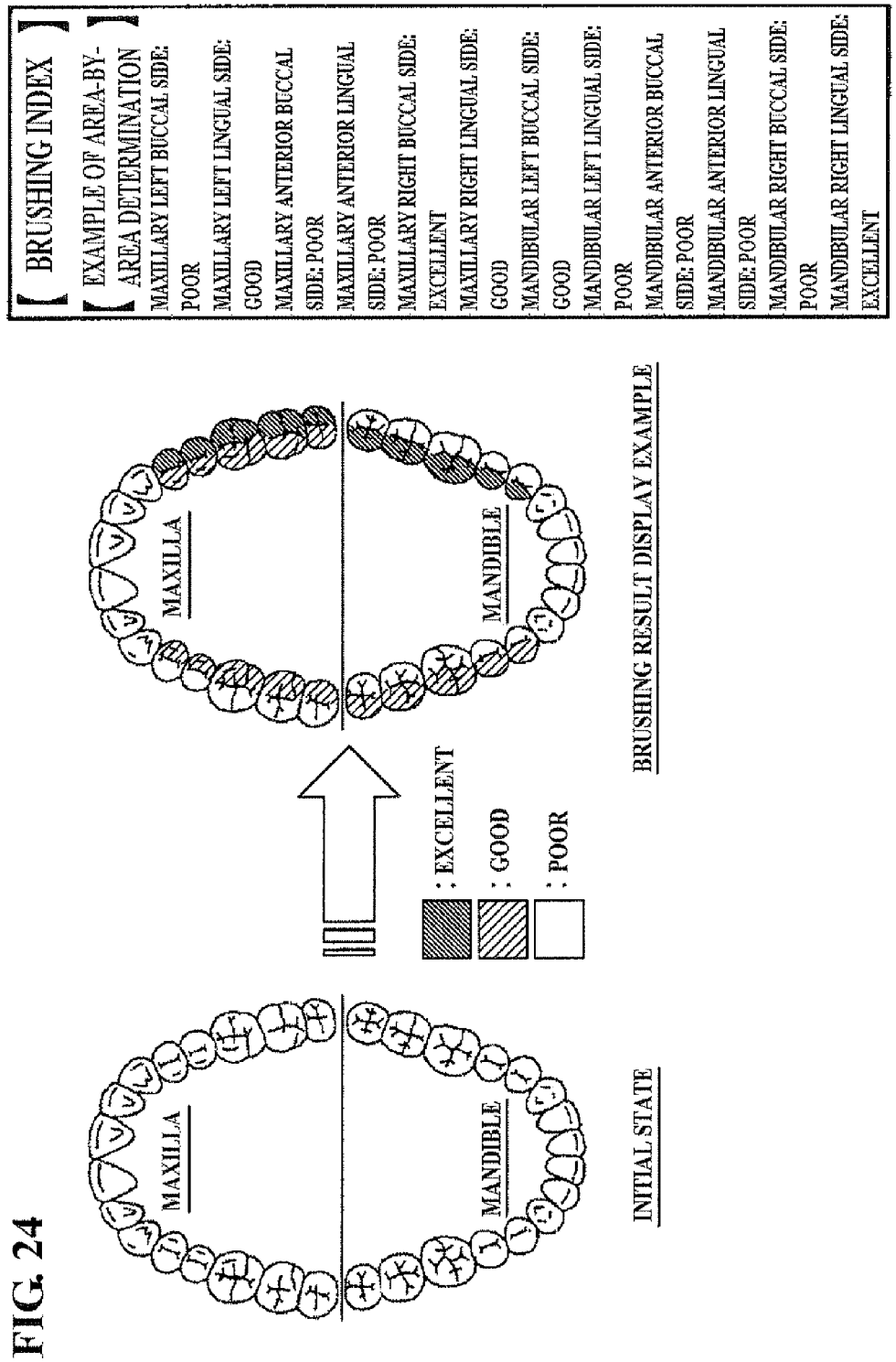
FIG. 24 is a diagram illustrating an example of the output of a brushing index serving as a brushing result.

FIG. 24 is an example of the output of an evaluation result for a brushing index. The brushing index is an index for collectively evaluating multiple evaluation items (brushing time, brush angle, and brush pressure), and indicates an achievement level for brushing. The formulas for calculating the brushing index may be defined in any manner. In the present embodiment, the brushing time and brush pressure are evaluated with a maximum of 35 points each and the brush angle is evaluated with a maximum of 30 points, and the total of those evaluation values (a maximum of 100 points) is used as the brushing index. In the example shown in FIG. 24, more than 80 points is called "excellent", 60 to 80 points is called "good", and less than 60 points is called "poor". Outputting this type of overall evaluation provides the user with more valuable guidelines.

According to the configuration described in the present embodiment thus far, using the outputs of the accelerometer 15 and the contact detection unit 50 make it possible to determine, with a high degree of precision, the orientation of the electric toothbrush 1 and whether or not the rear surface of the brush portion 3 is making contact with the body. As a result, it is possible to identify brushing areas with a higher degree of precision than in the past. Therefore, brushing results can be evaluated for more detailed segments (areas) than in the past, and useful and reliable evaluation guidelines can be provided to the user. Furthermore, the present embodiment is advantageous in that the accelerometer 15 is small and can thus easily be incorporated into the main body of the electric toothbrush. Further still, the electrodes 521 and 522 involve simpler wiring schemes than the cameras, temperature sensors, or distance sensors of the past, which makes it possible to reduce the size of the brush portion 3 (the brush head). Finally, the resistance to being soiled, to vibrations, and so on is also increased.

Note that the evaluation results from FIGS. 21 to 24 may be displayed simultaneously in the display 111, or may be displayed in sequence. In the case of the latter, the display may be switched automatically, or may be switched through the user manipulating a button.

Furthermore, in the above embodiment, the results are automatically displayed when the electric toothbrush 1 is turned off. However, because it can be assumed that brushing may be carried out in a different location than where the display device 110 is installed, it is preferable, for example, to provide a function so that the brushing information is sent to the display device 110 from the toothbrush main body 2 when the user presses a button provided in the display device 110 or the toothbrush main body 2 and the results are then displayed in the display device 110.

It is preferable for the brushing information, evaluation results, and so on accumulated in the memory 121 to be printable. For example, a printer (not shown) may be provided in the charger, the display device, or the like, or the configuration may be such that print data can be transmitted to an external printer from the toothbrush main body, the charger, the display device, and so on. Furthermore, it is preferable to provide a function for transferring data such as the brushing information, evaluation results, or the like to an external device (a personal computer, a mobile telephone, a PDA (personal digital assistant), or the like) (not shown) through wireless communication or hard-wired communication. In addition, a memory card slot (not shown) may be provided in the toothbrush main body, the charger, the display device, or the like, and data such as the brushing information, evaluation results, or the like may then be capable of being recorded in an external memory card.

In addition, the configuration may be such that optimum values (target values) for the brushing time, brush angle, and brush pressure can be set to different values on an area-by-area basis. For example, although a brush angle of 35° to 55° is preferable in order for the tips of the bristles to effectively remove food residue, plaque, or the like from the periodontal pockets, from between the teeth, and so on when brushing the tooth surfaces (side surfaces) of the molars, a greater angle (for example, 55° to 90°) is preferable when brushing the front teeth, which have comparatively larger tooth surfaces. Meanwhile, a brush angle of approximately 0° is preferable for the occlusal surfaces of the molars. Furthermore, the optimum brushing time, brush angle, and brush pressure can also be determined in view of avoiding damaging structures such as the gums, rather than in view of the effectiveness of cleaning. More useful and reliable evaluation guidelines can be provided if evaluation is carried out having determined the optimum values on an area-by-area basis in such a manner.

Variation

Although the aforementioned first embodiment describes the electric toothbrush as estimating areas during brushing and outputting brushing results on an area-by-area basis, instead of or in addition to this, the operating mode may be switched in accordance with the estimated area.

Figure 25:
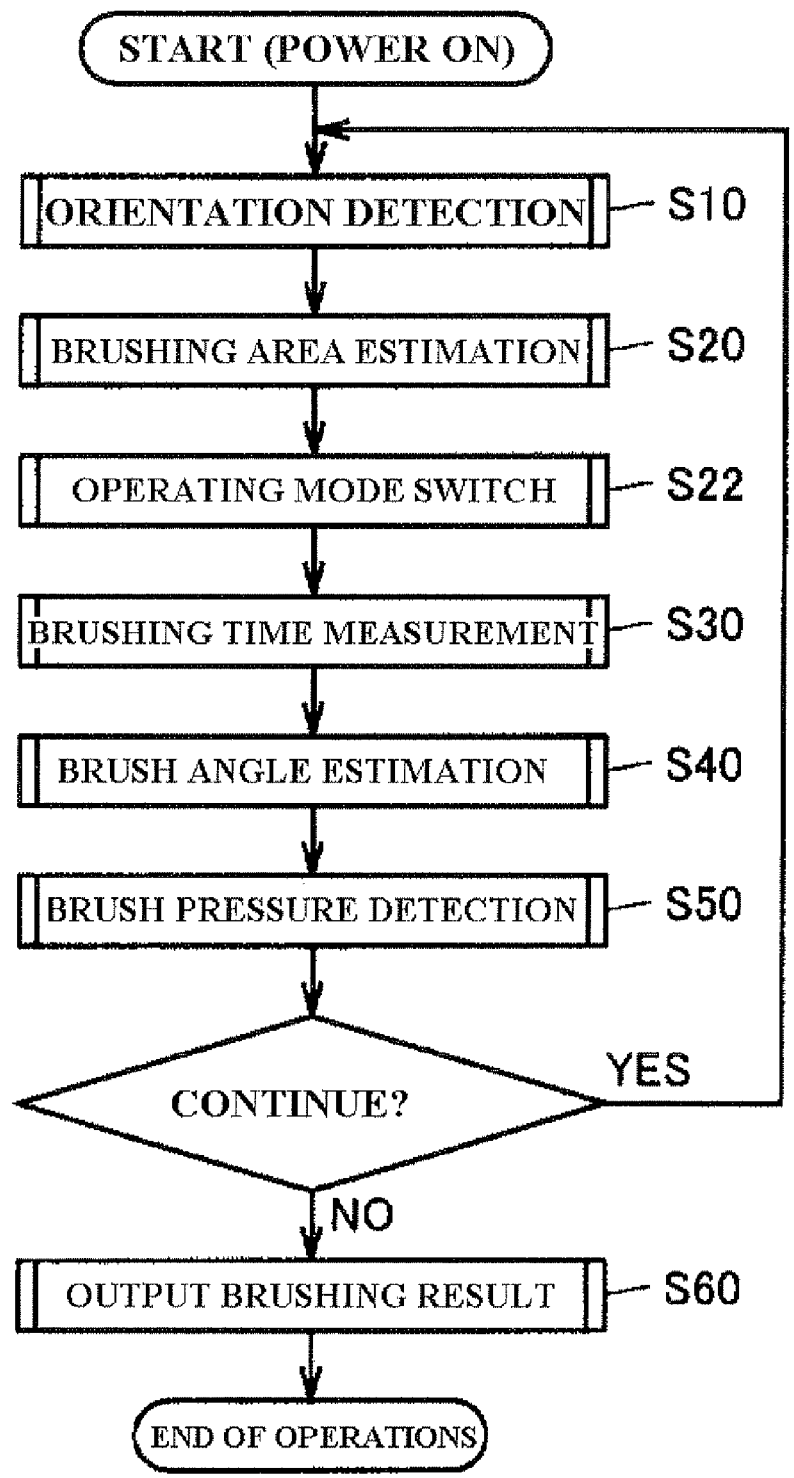
FIG. 25 is a flowchart illustrating a brushing evaluation process according to a variation on the first embodiment.

FIG. 25 is a flowchart illustrating a brushing evaluation process according to a variation on the first embodiment.

The only difference between this variation and the first embodiment is that an operating mode switching process (S22) is inserted between the brushing area estimation process (S20) and the brushing time measurement process (S30).

In the present variation, when the brushing area is estimated (S20), the operating mode switching process is executed (S22). A method such as that disclosed in the aforementioned JP-2009-240759A can be employed as the operating mode switching process. Specifically, the rotation direction of the motor (forward/reverse) may be switched in accordance with the brushing area. The effectiveness of plaque removal can be improved by controlling the rotation direction of the motor and causing the tips of the bristles to move appropriately and effectively for the brushing area. Alternatively, the rotational frequency of the motor may be switched in accordance with the brushing area. The effectiveness of plaque removal can be improved by controlling the rotational frequency of the motor and causing the tips of the bristles to move appropriately and effectively for the brushing area.

Second Embodiment

In the first embodiment, the brushing area is determined from among the twelve areas illustrated in FIG. 5. In the second embodiment, the brushing areas are detected at an even more detailed level than the brushing areas determined according to the segmentation shown in FIG. 5.

The basic configuration and operations of the electric toothbrush according to the present embodiment are the same as those in the first embodiment. Accordingly, the following will describe in detail only the differences from the first embodiment.

Figure 26:
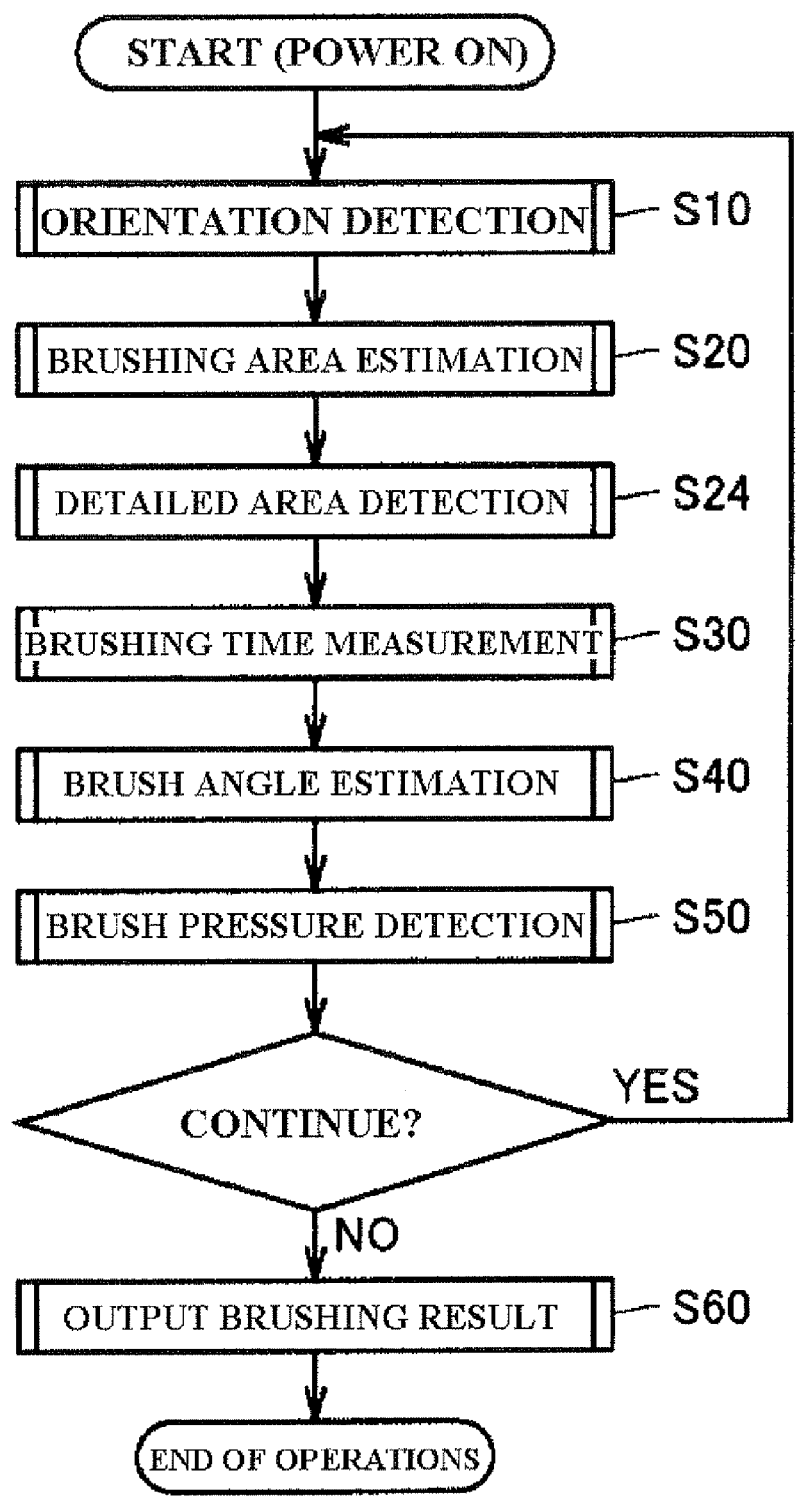
FIG. 26 is a flowchart illustrating a brushing evaluation process according to a second embodiment.

FIG. 26 is a flowchart illustrating a brushing evaluation process according to the second embodiment.

As shown in FIG. 26, the only difference between this embodiment and the first embodiment is that a detailed area detection process (S24) is inserted between the brushing area estimation process (S20) and the brushing time measurement process (S30).

In order to detect areas at a detailed level, the electric toothbrush according to the present embodiment further includes, in addition to the electrodes 521 and 522 described in the first embodiment, at least one electrode, located in an area aside from the rear surface of the brush portion 3, for detecting contact at locations within the mouth that can be entered into during brushing.

Figure 27:
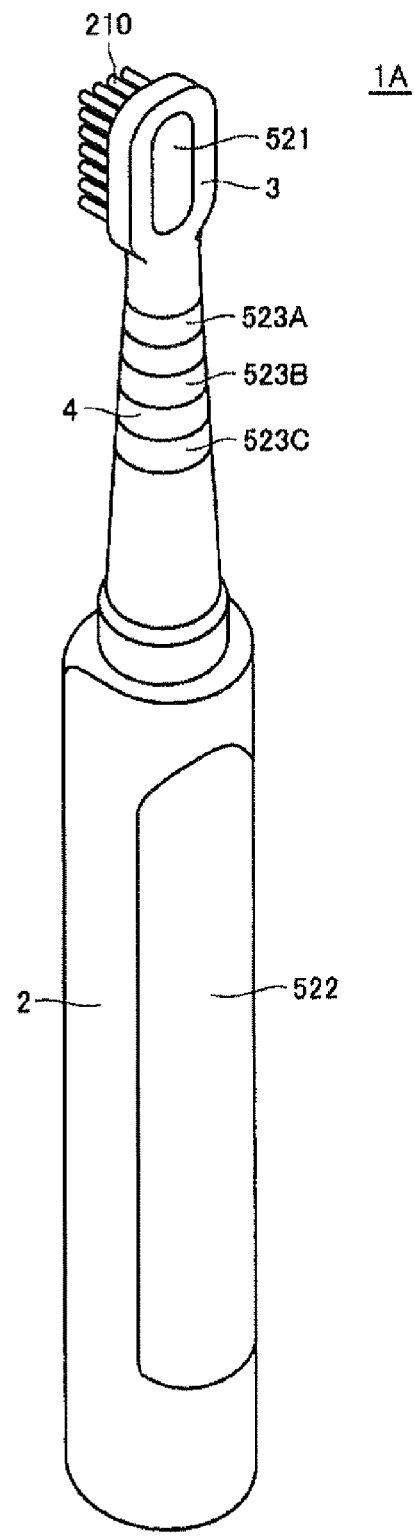
FIG. 27 is a perspective view illustrating an example of the external appearance of an electric toothbrush according to the second embodiment.

FIG. 27 is a perspective view illustrating an example of the external appearance of an electric toothbrush 1A according to the second embodiment.

As shown in FIG. 27, the electric toothbrush 1A further includes three electrodes (also called "shank electrodes" hereinafter) 523A, 523B, and 523C disposed on the shank portion 4. In other words, according to the present embodiment, the electrode portion 52 in the contact detection unit 50 shown in FIG. 1 includes the rear surface electrode 521 disposed on the rear surface of the brush portion 3, the main body electrode 522 disposed on the main body 2, and the shank electrodes 523A, 523B, and 523C. The detection portion 54 detects the impedances of the shank electrodes 523A, 523B, and 523C.

It is desirable for the shapes of the electrodes 523A, 523B, and 523C to be, for example, ring shapes, in order to detect brushing areas regardless of the brush angle.

The detailed area detection process (S24) will be described with reference to FIGS. 28 and 29.

Figure 28:
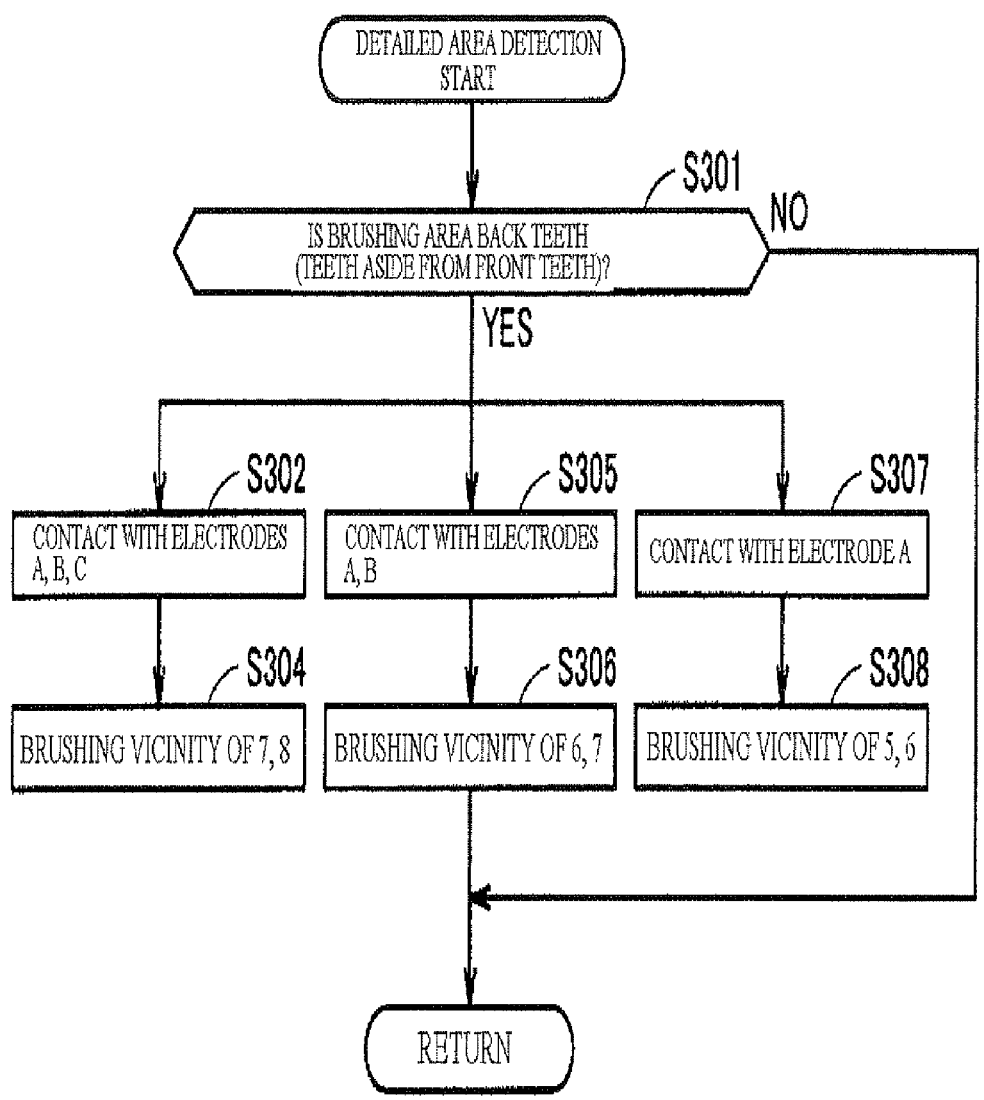
FIG. 28 is a flowchart illustrating a detailed area detection process according to the second embodiment.
Figure 29:
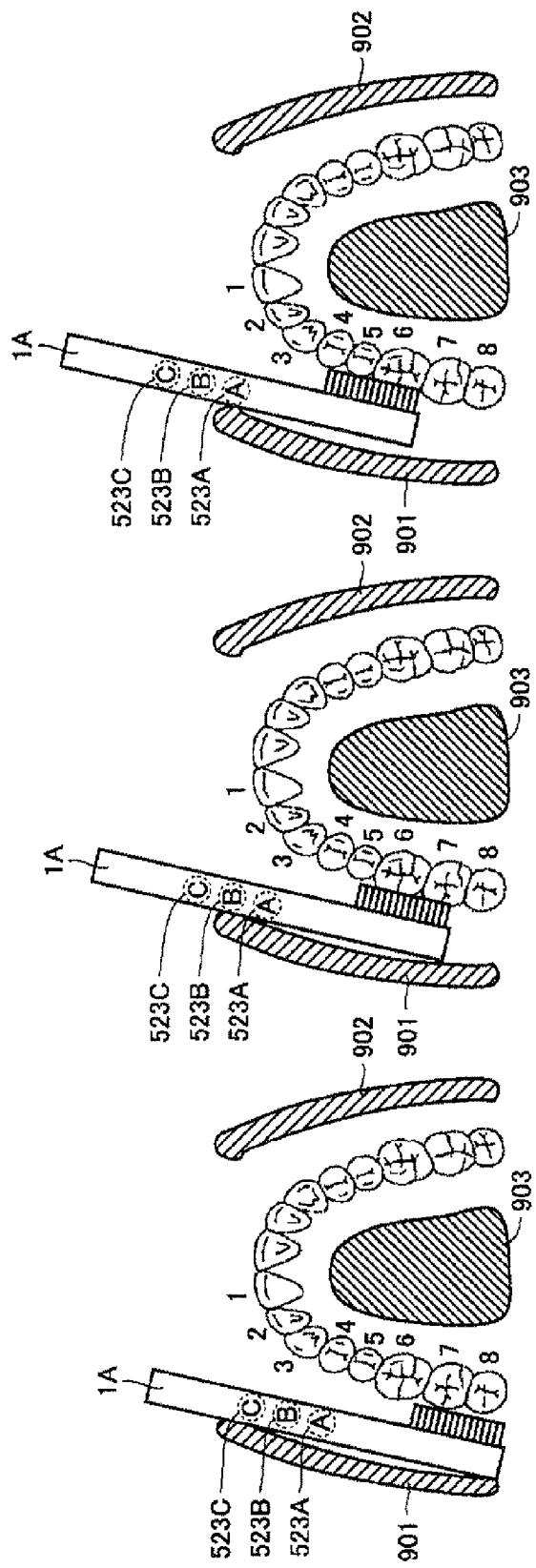
FIGS. 29A, 29B, and 29C are diagrams illustrating a method for detecting a detailed area using shank electrodes.

FIG. 28 is a flowchart illustrating the detailed area detection process (824). FIGS. 29A, 2913, and 29C are diagrams illustrating a method for detecting a detailed area using the shank electrodes. Note that in FIGS. 28 and 29, the shank electrodes 523A, 523B, and 523C are also indicated as electrodes A, B, and C, respectively.

In the present embodiment, the detailed areas are detected when the brushing area is located in the back teeth (that is, the teeth aside from the front teeth).

Referring to FIG. 29A, it is assumed, for example, that the estimated brushing area is the mandibular right buccal side. In this case, the electrodes A, B, and C all make contact with the body (the inside of a right cheek 901) when back teeth 7 and 8 (the teeth that are furthest back) are being brushed. Meanwhile, as shown in FIG. 29B, the electrodes A and B make contact with the body when back teeth 6 and 7 are being brushed. Finally, as shown in FIG. 29C, the electrode A, which is located closest to the brush, makes contact with the body when back teeth 5 and 6 (the teeth closest to the front) are being brushed.

Detailed areas (teeth) can also be identified when brushing the brushing areas of other back teeth by detecting which of the electrodes A, B, and C are making contact with the inside of a left cheek 902 or with a tongue 903.

As shown in FIG. 28, first, the CPU 120 determines whether or not the brushing area estimated in S20 corresponds to back teeth (that is, teeth aside from the front teeth) (S301). If the estimated brushing area corresponds to front teeth instead of back teeth (NO in S301), the process ends. However, if the estimated brushing area corresponds to back teeth (YES in S301), it is determined which electrodes are making contact with the body by detecting the impedances of the electrodes A, B, and C (the shank electrodes 523A, 523B, and 523C).

In the case where it has been determined that all the electrodes A, B, and C are making contact (S302), it is determined that the vicinity of the back teeth 7 and 8 is being brushed (S304). Meanwhile, in the case where it has been determined that the electrodes A and B are making contact (S305), it is determined that the vicinity of the back teeth 6 and 7 is being brushed (S306). Finally, in the case where it has been determined that only the electrode A is making contact (S307), it is determined that the vicinity of the back teeth 5 and 6 is being brushed (S308).

Note that the method for determining whether or not contact is being made with the body may be switched depending on whether the brushing area corresponds to the buccal side or the lingual side, For example, the same concept as with the method for determining the buccal side/lingual side according to the first embodiment may be employed. In other words, for the back teeth on the buccal side, it may be determined that contact is being made if the percentage of time for which the impedance is less than a threshold is greater than or equal to 80%, whereas for the back teeth on the lingual side, it may be determined that contact is being made if the percentage of time for which the impedances less than the threshold is 30 to 80%.

Thus, according to the second embodiment as described thus far, more detailed brushing areas can be detected than in the first embodiment, and thus more detailed brushing results can be outputted.

Although three shank electrodes are provided in the present embodiment, it should be noted that the configuration may be such that only one shank electrode, corresponding to, for example, the electrode B or C, is provided. This is because even with only a single shank electrode, it is possible to detect whether or not that shank electrode is making contact with the body, which in turn makes it possible to generally determine whether the tooth is further back or further forward.

Variation

In the aforementioned second embodiment, shank electrodes are provided in the electric toothbrush in order to detect areas at a more detailed level in the case where the brushing area corresponds to the back teeth. In this variation, areas are detected at a more detailed level in the case where the brushing area corresponds to the front teeth.

Figure 30:
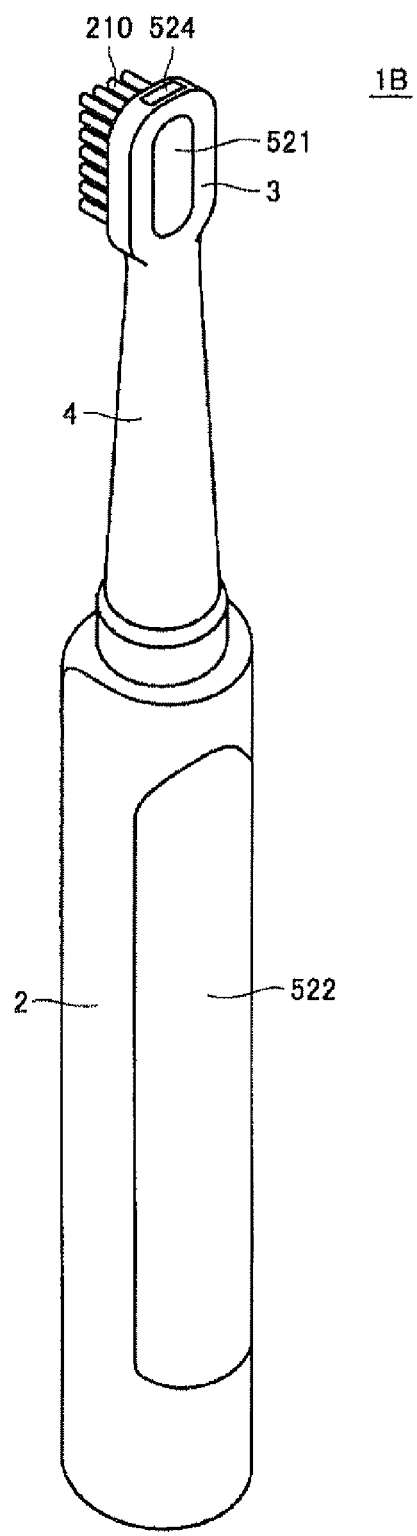
FIG. 30 is a perspective view illustrating an example of the external appearance of an electric toothbrush according to a variation on the second embodiment.

FIG. 30 is a perspective view illustrating an example of the external appearance of an electric toothbrush, 1B according to a variation on the second embodiment.

As shown in FIG. 30, in the present variation, the electric toothbrush 1B further includes an electrode (also called a "distal end electrode") 524 on the distal end area of the brush portion 3. In other words, in the present variation, the electrode portion 52 in the contact detection unit 50 shown in FIG. 1 includes the rear surface electrode 521 disposed on the rear surface of the brush portion 3, the main body electrode 522 disposed on the main body 2, and the distal end electrode 524. The detection portion 54 also detects the impedance of the distal end electrode 524.

The detailed area detection process (S24) according to the present variation will be described with reference to FIGS. 31 and 32.

Figure 31:
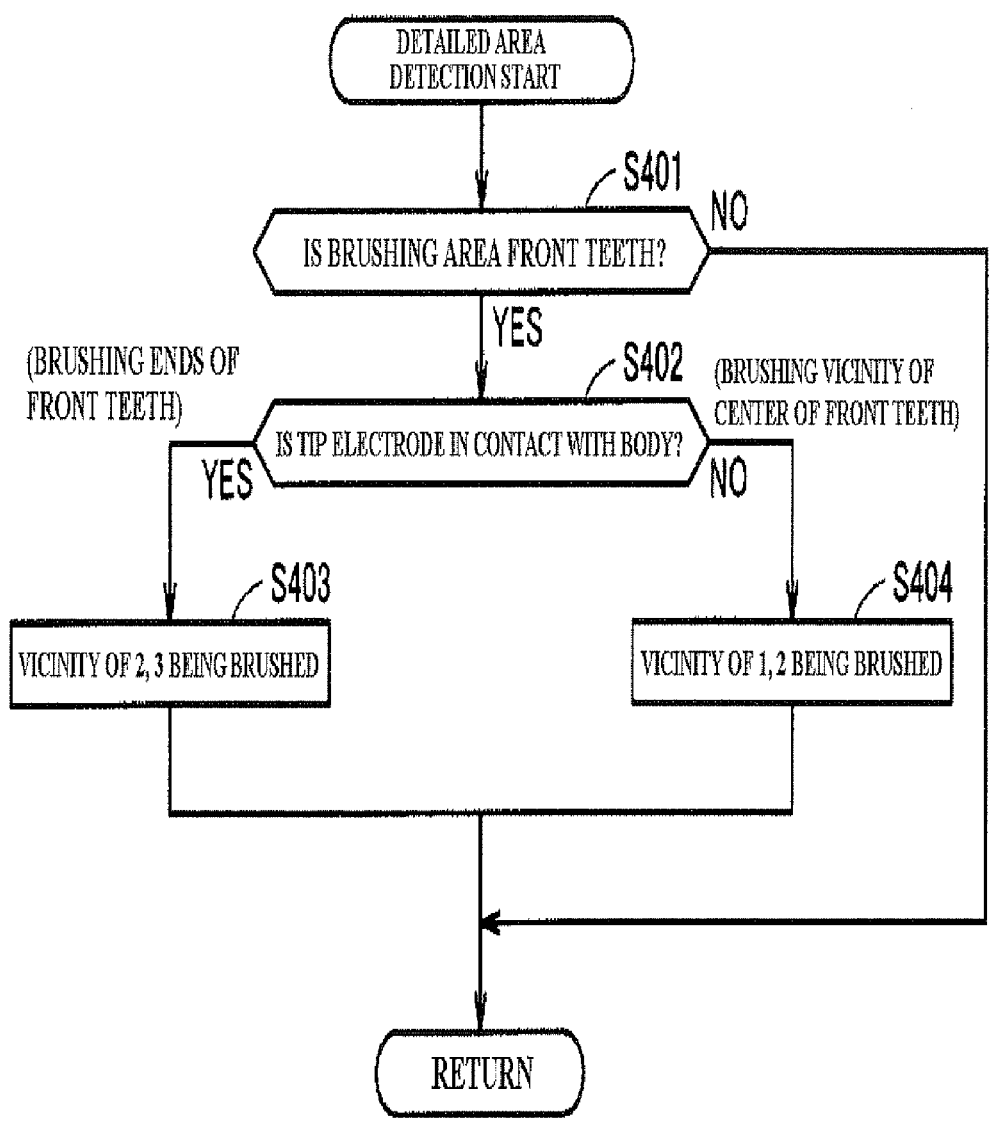
FIG. 31 is a flowchart illustrating a detailed area detection process according to a third embodiment.

FIG. 31 is a flowchart illustrating the detailed area detection process (S24). FIG. 32 is a diagram illustrating a method for detecting a detailed area using the distal end electrode.

Figure 32:
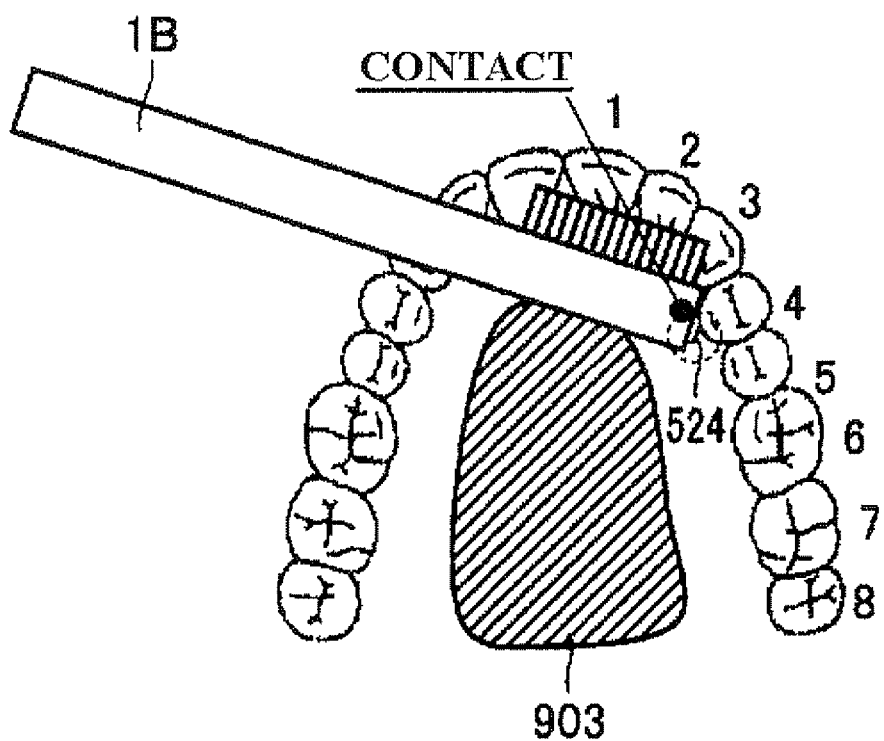
FIG. 32 is a diagram illustrating a method for detecting a detailed area using a distal end electrode.

Referring to FIG. 32, it is assumed, for example, that the estimated brushing area is the maxillary anterior lingual side (the maxillary anterior palatal side). In this case, the distal end electrode 524 does not make contact with the body (teeth) when brushing in the vicinity of front teeth 1 and 2, but the distal end electrode 524 does make contact with the body (teeth) when brushing in the vicinity of front teeth 2 and 3.

Detailed areas (teeth) can also be identified when brushing the brushing areas of other front teeth by detecting whether the distal end electrode 524 is making contact with the front teeth on the inner buccal side or on the opposite side as the front teeth 1 through 3 shown in FIG. 32.

As shown in FIG. 31, first, the CPU 120 determines whether or not the brushing area estimated in S20 corresponds to front teeth (S401). If the brushing area corresponds to back teeth instead of front teeth (NO in S401), the process ends. However, if the estimated brushing area corresponds to front teeth (YES in S401), it is determined whether or not the distal end electrode 524 is making contact with the body by detecting the impedance of the distal end electrode 524 (S402).

In the case where it has been determined that the distal end electrode 524 is making contact with the body (YES in S402), it is estimated that an end of the front teeth is being brushed, and thus it is determined that the vicinity of the front teeth 2 and 3 is being brushed (S403). On the other hand, in the case where it has been determined that the distal end electrode 524 is not making contact with the body (NO in S402), it is estimated that the vicinity of the center of the front teeth is being brushed, and thus it is determined that the vicinity of the front teeth 1 and 2 is being brushed (S404).

Thus, according to the present variation, more detailed brushing areas can be detected than in the first embodiment, and thus more detailed brushing results can be outputted.

Third Embodiment

The electric toothbrush according to the present embodiment further includes a function for correcting brushing areas estimated using the accelerometer and rear surface electrode as described in the first embodiment.

The basic configuration and operations of the electric toothbrush according to the present embodiment are the same as those in the first embodiment. Accordingly, the following will describe in detail only the differences from the first embodiment.

Figure 33:
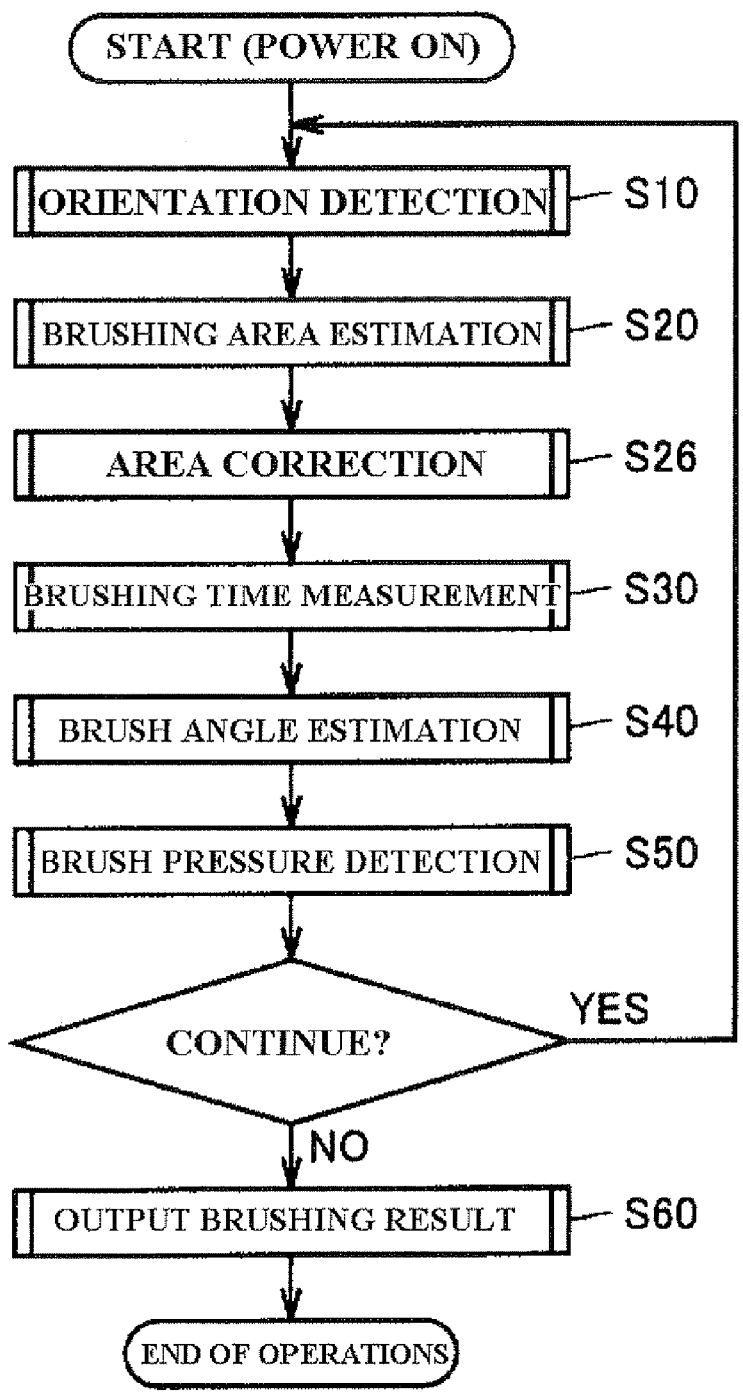
FIG. 33 is a flowchart illustrating a brushing evaluation process according to the third embodiment.

FIG. 33 is a flowchart illustrating a brushing evaluation process according to the third embodiment.

As shown in FIG. 33, the only difference between this embodiment and the first embodiment is that an area correction process (S26) is inserted between the brushing area estimation process (S20) and the brushing time measurement process (S30).

Figure 34:
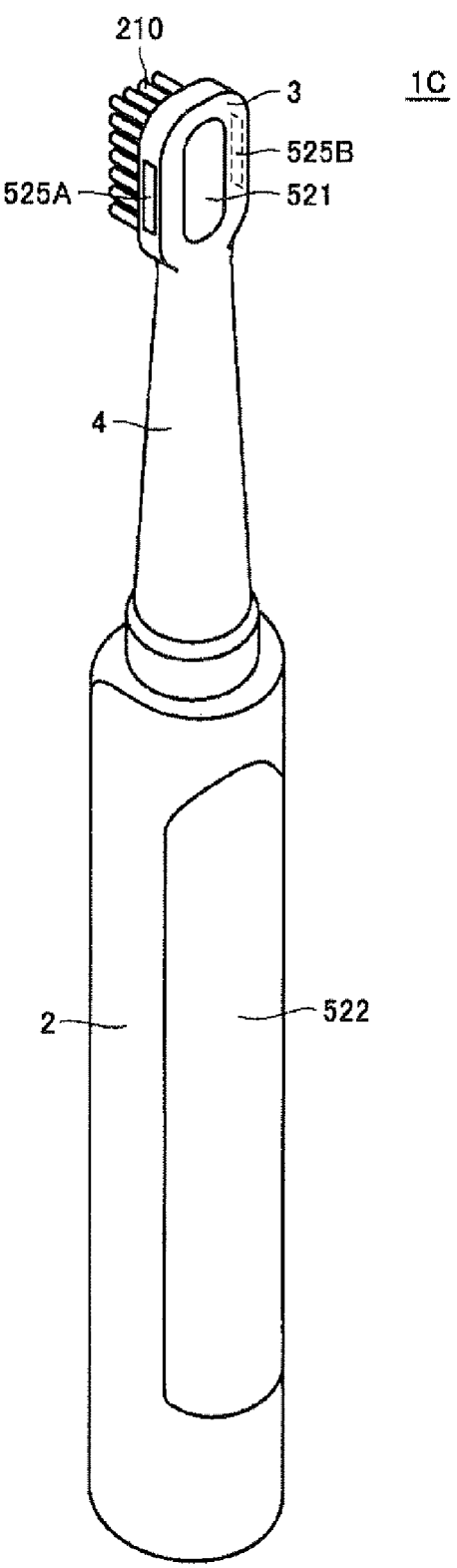
FIG. 34 is a perspective view illustrating an example of the external appearance of an electric toothbrush according to the third embodiment.

FIG. 34 is a perspective view illustrating an example of the external appearance of an electric toothbrush 1C according to the third embodiment.

As shown in FIG. 34, in the electric toothbrush 1C, electrodes (also called "side-surface electrodes" hereinafter) 525A and 525B are further disposed on both sides of the brush portion 3. In other words, according to the present embodiment, the electrode portion 52 in the contact detection unit 50 shown in FIG. 1 includes the rear surface electrode 521 disposed on the rear surface of the brush portion 3, the main body electrode 522 disposed on the main body 2, and the side-surface electrodes 525A and 525B. The detection portion 54 also detects the impedances of the side-surface electrodes 525A and 525B.

In the case where the brush surface (that is, the surface in which the bristles 210 are present) corresponds to the front surface, the side-surface electrode 525A is located on the right side surface and the side-surface electrode 525B is located on the left side surface.

Figure 35:
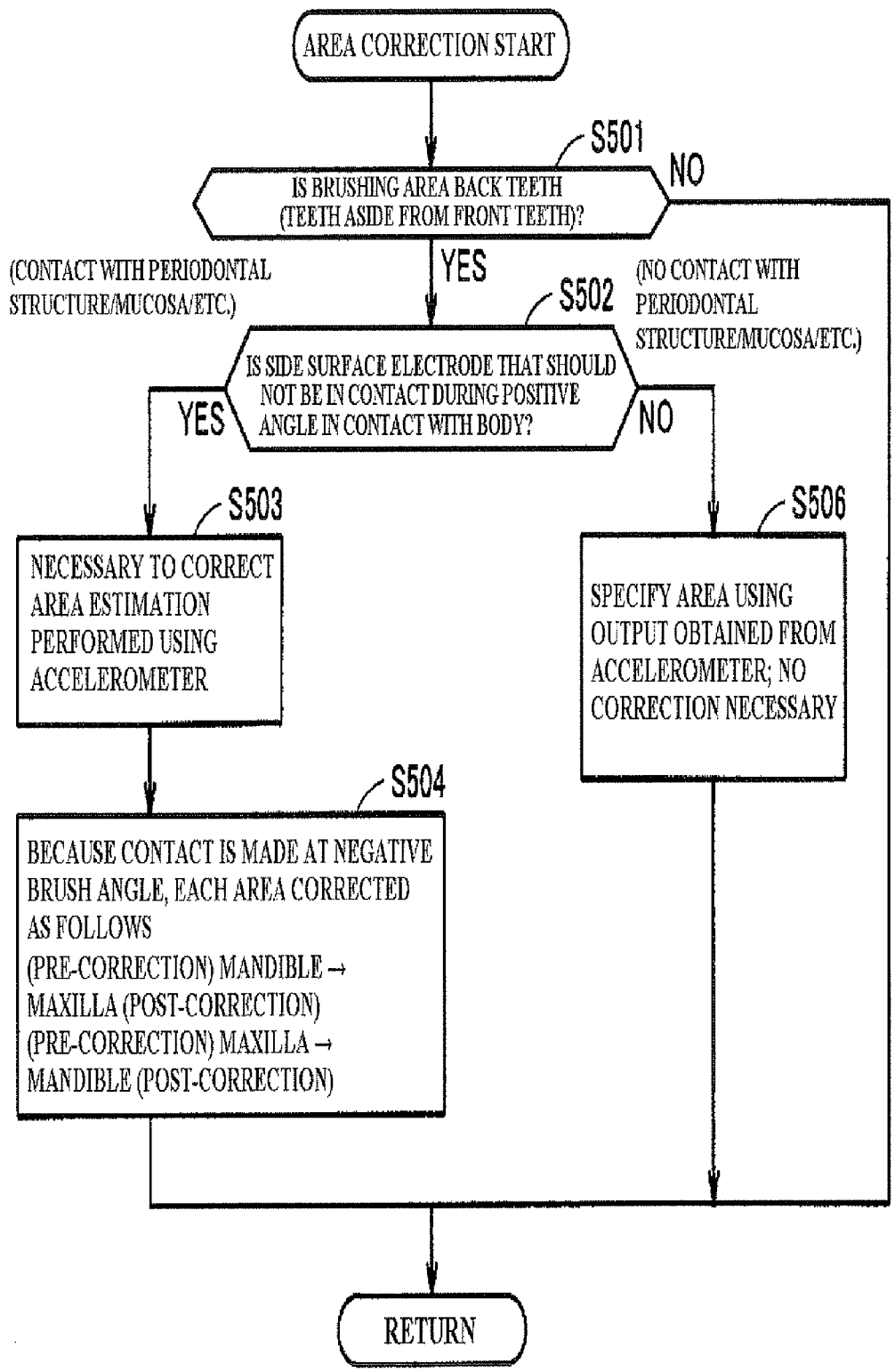
FIG. 35 is a flowchart illustrating an area correction process according to the third embodiment.
Figure 36:
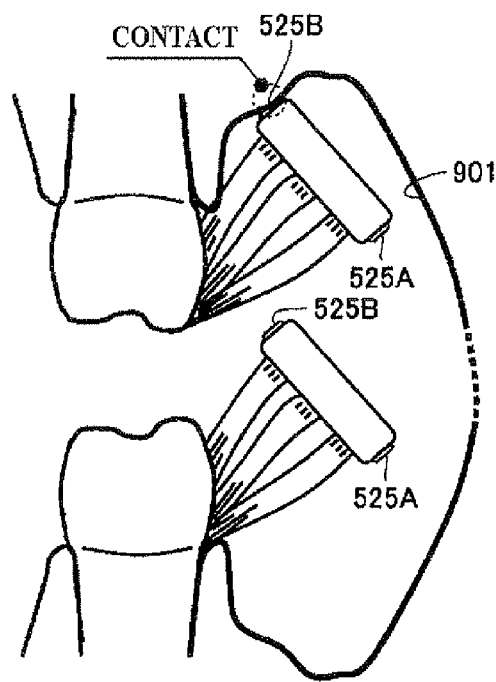
FIG. 36 is a diagram illustrating an area correction method that uses side-surface electrodes.

FIG. 35 is a flowchart illustrating the area correction process (S26). FIG. 36 is a diagram illustrating an area correction method that uses the side-surface electrodes.

In the present embodiment, the detailed areas are detected when the brushing area is located in the back teeth (that is, the teeth aside from the front teeth).

FIG. 36 schematically illustrates teeth on the right side as seen from inside the mouth. In the case where the brushing area corresponds to a right back tooth and an upper tooth is being brushed, the side-surface electrode 52513 on the left side can make contact with the body (with the periodontal structures, mucosa, and so on on the right cheek 901 side), but the side-surface electrode 525A on the right side does not make contact with the body. In other words, when brushing the upper back teeth, the side-surface electrode 525B is not in contact with the body when the brush angle corresponds to a positive angle, but can come into contact with the body when the brush angle corresponds to a negative angle. On the other hand, when the lower teeth are being brushed, the side-surface electrode 525A on the right side can make contact with the body, but the side-surface electrode 525B on the left side does not make contact with the body. In other words, when brushing the lower back teeth, the side-surface electrode 525A is not in contact with the body when the brush angle corresponds to a positive angle, but can come into contact with the body when the brush angle corresponds to a negative angle.

Figure 37:
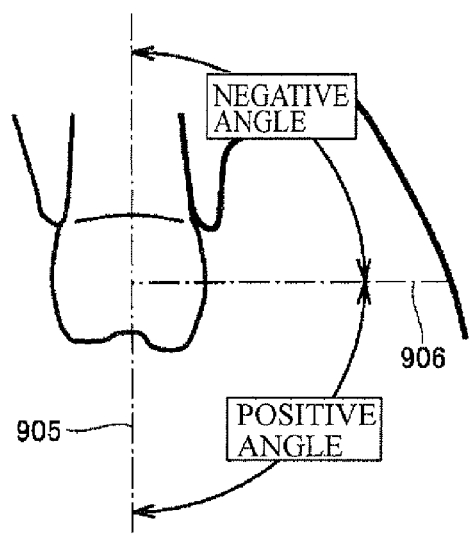
FIG. 37 is a diagram illustrating brush angles.

FIG. 37 is a diagram illustrating brush angles. As shown in FIG. 37, in the present embodiment, the direction when the bristle tips face toward the periodontal pocket from a perpendicular position 906 relative to a tooth axis 905 is called a "positive angle", whereas the direction when the bristle tips face away from the periodontal pocket from the perpendicular position 906 relative to the tooth axis 905 is called a "negative angle". Therefore, the orientation of the lower toothbrush in FIG. 36 indicates a positive angle, whereas the orientation of the upper toothbrush in FIG. 36 indicates a negative angle.

As shown in FIG. 35, first, the CPU 120 determines whether or not the brushing area estimated in S20 corresponds to back teeth (that is, teeth aside from the front teeth) (S501). If the brushing area corresponds to the front teeth instead of the back teeth (NO in S501), the process ends. However, if the estimated brushing area corresponds to back teeth (YES in S501), it is determined which electrodes are making contact with the body by detecting the impedances of the side-surface electrodes 525A and 525B.

It is then determined whether or not the side-surface electrode that should not be in contact for the estimated brushing area is making contact with the body (S502). Specifically, if, for example, the estimated brushing area is the mandibular right buccal side, the side-surface electrode 525B on the left side should not be in contact, as shown in FIG. 36. Therefore, when the estimated brushing area is the mandibular right buccal side, it is determined whether or not the side-surface electrode 525B on the left side has made contact. On the other hand, if the estimated brushing area is the maxillary right buccal side, the side-surface electrode 525A on the right side should not be in contact, as shown in FIG. 36. Therefore, when the estimated brushing area is the maxillary right buccal side, it is determined whether or not the side-surface electrode 525A on the right side has made contact.

If the side-surface electrode that should not be in contact is not in contact with the body (NO in S502), it is determined that it is necessary to identify the area based on the output obtained from the accelerometer 15, or in other words, that it is not necessary to correct the area (S506).

However, in the case where it has been determined that the side-surface electrode that should not be in contact has made contact with the body (YES in S502), it is determined that it is necessary to correct the area identified by the accelerometer 15 (S503). In other words, in this case, the brush angle corresponds to a negative angle and contact is made with the body, and thus the CPU 120 carries out correction that inverts the mandible and maxilla for each area (S504).

In this manner, the brushing areas can be identified with certainty by using the side-surface electrodes in the case where there is an error in the brushing area determined using the accelerometer 15.

Fourth Embodiment

Although brushing areas are identified by detecting contact with the body using one or more electrodes in the aforementioned first through third embodiments, the electrode specifications are not limited as long as the device used for detecting contact with the body is an electrode-based device.

The basic configuration and operations of the electric toothbrush according to the present embodiment are the same as those in the first embodiment. Accordingly, the following will describe in detail only the differences from the first embodiment.

In the present embodiment, the contact detection unit 50 shown in FIG. 1 includes an electrode portion 53 that configures an electrostatic capacitance-type sensor and a detection portion 55 for detecting changes in the electrostatic capacitance of the electrode portion 53, instead of the electrode portion 52 and the detection portion 54, respectively.

Figure 38:
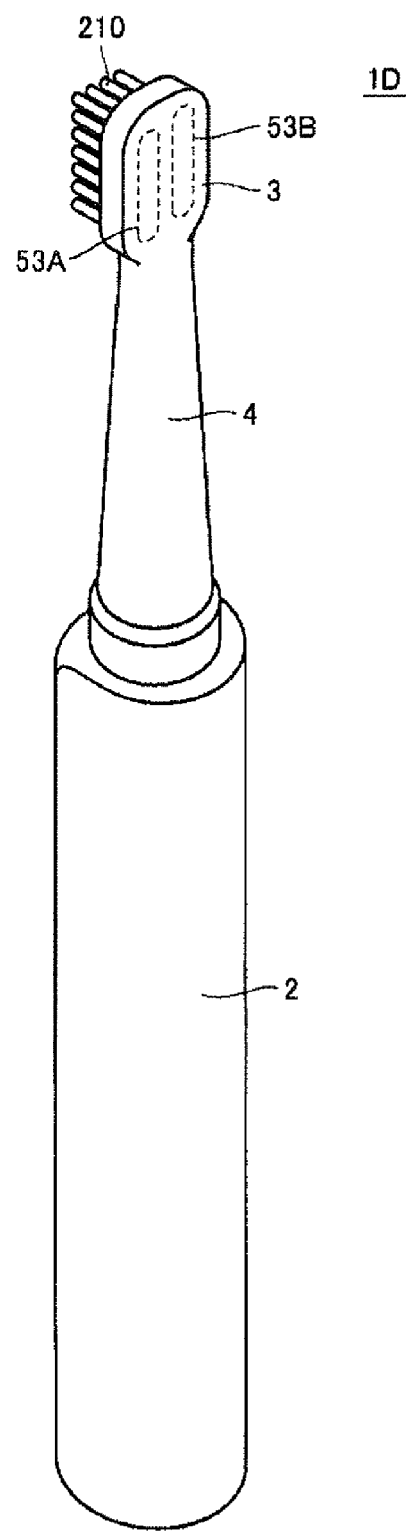
FIG. 38 is a perspective view illustrating an example of the external appearance of an electric toothbrush according to a fourth embodiment.

FIG. 38 is a perspective view illustrating an example of the external appearance of an electric toothbrush 1D according to the fourth embodiment.

As shown in FIG. 38, the electric toothbrush 1D includes, on the rear surface side of the brush, portion 3, a pair of electrodes (conductors) 53A and 53B, serving as electrostatic capacitance-type sensor components. As in the first embodiment, the detection portion 55 may be installed within the driving circuit 12, as shown in FIG. 3. Note that because an electrostatic capacitance-type sensor does not employ impedance detection as in the other embodiments, an electrode need not be provided on the side of the main body 2 that makes contact with the user's hand.

Figure 39:
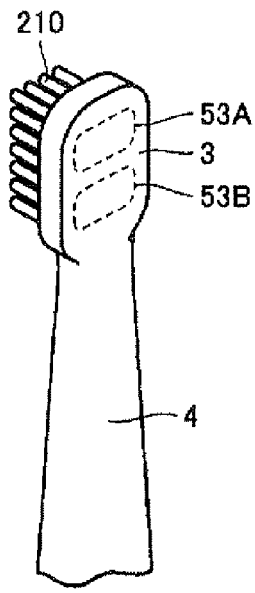
FIG. 39 is a diagram illustrating an example of another layout of a pair of electrodes according to the fourth embodiment.

The electrodes 53A and 53B are, for example, cylindrical members configured of copper, SUS, or the like. The electrodes 53A and 53B are disposed within a cavity in the brush portion 3, with the axial direction of the toothbrush serving as the lengthwise direction thereof. In addition, the electrodes 53A and 53B are disposed so as to be adjacent to each other in the horizontal direction with a predetermined gap provided therebetween. Note that the locations in which the electrodes 53A and 53B are disposed are not limited to the locations illustrated in FIG. 38. For example, as shown in FIG. 39, the electrodes 53A and 53B may be disposed adjacent to each other in the vertical direction, with the direction perpendicular to the axial direction of the toothbrush serving as the lengthwise direction thereof.

The pair of electrodes 53A and 53B are connected to the detection portion 55 via lead wires (not shown) in a state in which the electrodes 53A and 53B are insulated from each other, and function as capacitors that accumulate electrical charges when voltages are applied thereto. The detection portion 55 detects an electrostatic capacitance between the electrodes 53A and 53B, converts the detected electrostatic capacitance into a frequency, and outputs the frequency to the CPU 120.

Here, a principle where the electrostatic capacitance produced between the electrodes 53A and 53B changes due to differences in the dielectric constants between the air and the body will be described.

Figure 40A:
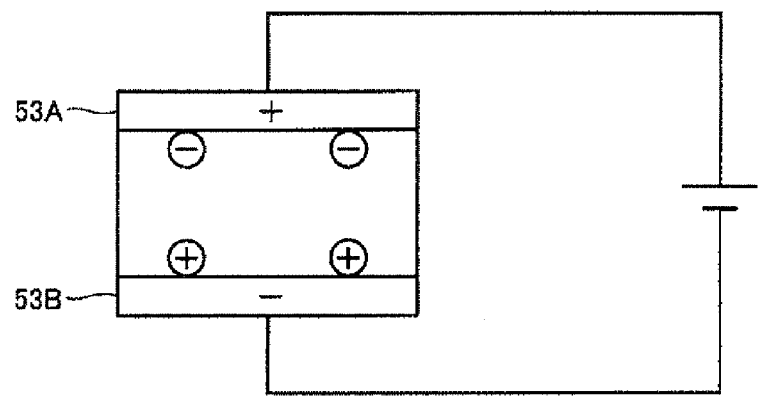
FIGS. 40A and 40B are diagrams illustrating a principle by which electrostatic capacitance between electrodes changes due to contact with a body.
Figure 40B:
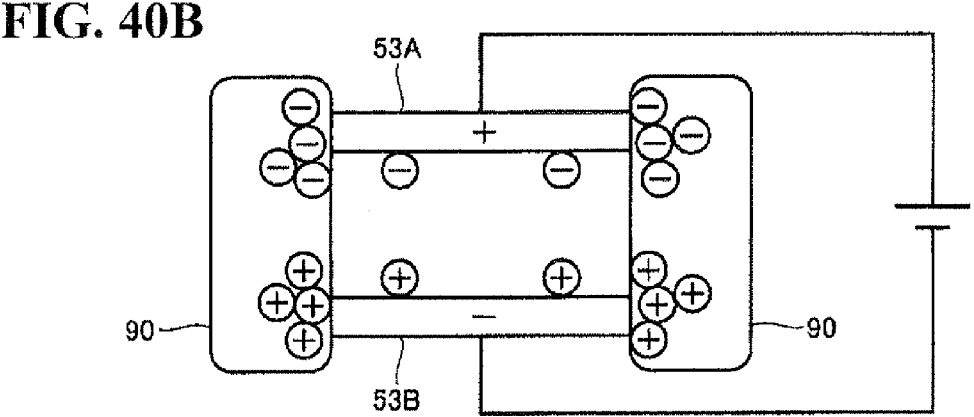

FIGS. 40A and 40B are diagrams illustrating the principle where the electrostatic capacitance between the electrodes 53A and 53B changes due to contact with the body. Although FIGS. 40A and 40B schematically illustrate a body 90 and the electrodes 53A and 53B as being in direct contact, it should be noted that in actuality, the exterior of the brush portion 3 is present between the two.

Because the relative dielectric constant of the body is greater than the relative dielectric constant of the air, a greater electrical charge is conducted to the regions of the body 90 in the vicinity of the electrodes than the air when the body 90 makes contact with the rear surface of the brush portion 3. As a result, the electrostatic capacitance increases between the electrodes 53A and 53B.

The CPU 120 determines whether or not the rear surface of the brush portion 3 is making contact with the body by measuring changes in the electrostatic capacitance converted to a frequency by the detection portion 55. Specifically, the CPU 120 can determine whether or not the rear surface of the brush portion 3 is making contact with the body by detecting, for example, whether or not the electrostatic capacitance has exceeded a threshold (unit: pF) set in advance through experimentation.

In this manner, in the case where an electrostatic capacitance-type sensor has been provided in the electric toothbrush, the electrodes of the sensor are not exposed on the exterior, which makes it possible to prevent a drop in the precision of contact detection caused by the influence of grime or the like, as compared to the case where electrodes that are exposed on the external surface are provided.

Furthermore, because the configuration does not have the electrodes come into direct contact with the body, no current flows directly into the body via the electrodes, which makes it possible to suppress the effects of direct electricity on the human body. Further still, in the case where the rear surface of the brush portion 3 is configured of, for example, a resin, the brush portion 3 that is configured of a resin serves as protection even if static electricity is applied to the toothbrush, which makes it possible to prevent internal components such as the CPU from being damaged by static electricity.

Note that the functions of the electrodes in the second and third embodiments aside from the rear surface electrode can also be realized by electrostatic capacitance-type sensors. In other words, the detection of detailed areas, the correction of areas, and so on may be realized by providing a pair of electrodes on the shank portion of the electric toothbrush, or on the distal end or side surfaces of the brush portion.

First Variation

Although the aforementioned fourth embodiment describes a configuration in which a pair of electrodes is provided as the configuration of the electrostatic capacitance-type sensor, the configuration may be such that only a single electrode is provided.

Figure 41:
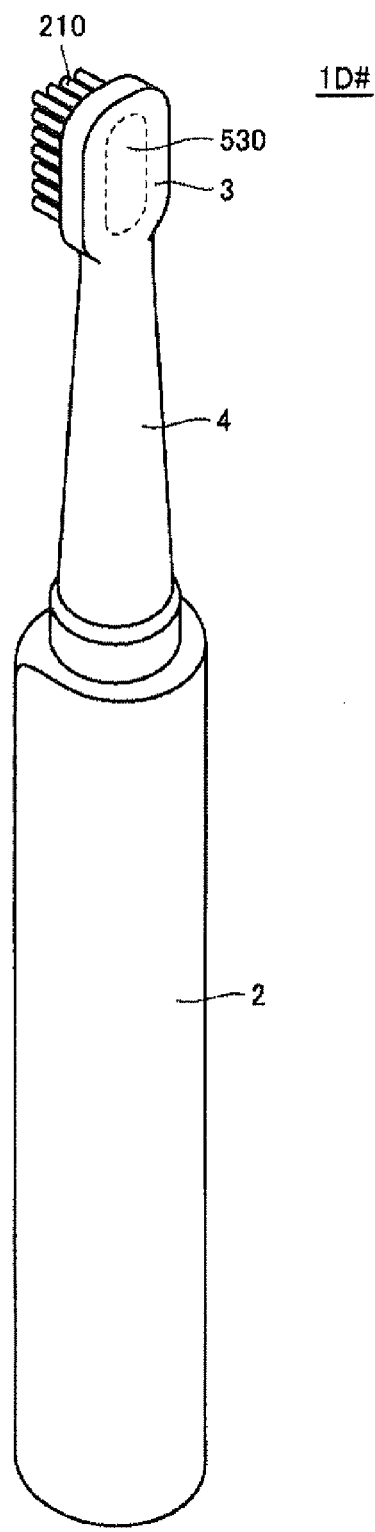
FIG. 41 is a perspective view illustrating an example of the external appearance of an electric toothbrush according to a first variation on the fourth embodiment.

FIG. 41 is a perspective view illustrating an example of the external appearance of an electric toothbrush 1D# according to a first variation on the fourth embodiment.

As shown in FIG. 41, the electric toothbrush 1D# includes, on the rear surface side of the brush portion 3, a single electrode (conductor) 530, serving as an electrostatic capacitance-type sensor component. In the present variation, the electrode 530 functions as one of the electrodes of a capacitor, and the body functions as the other electrode of the capacitor.

Figure 42:
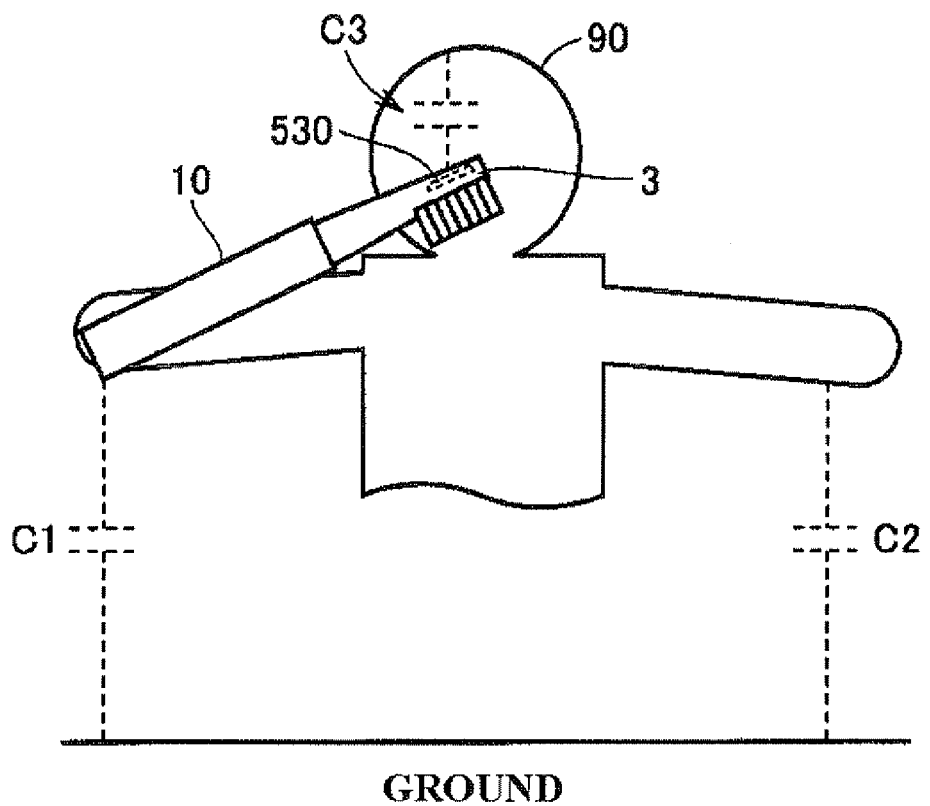
FIG. 42 is a schematic diagram illustrating a principle by which contact is detected according to the first variation on the fourth embodiment.

FIG. 42 is a schematic diagram illustrating a principle by which contact is detected according to the first variation on the fourth embodiment.

As shown in FIG. 42, when the brush portion 3 of the electric toothbrush 1D# makes contact with the cheek mucosa, tongue, or the like of the body 90, a circuit is formed, as shown in the diagram, between the electric toothbrush 1D#, the body 90, and the ground. At this time, electrostatic capacitances C1, C2, and C3 are formed between the electric toothbrush 1D# and the ground, the body 90 and the ground, and the body 90 and the electrode 530, respectively. The combined capacitance Cx of this circuit is expressed as $1/C_x=1/C_1+1/C_2+1/C_3$. The electrostatic capacitance C3 between the body 90 and the electrode 530 increases when the cheek mucosa, tongue, or the like of the body 90 makes contact with the rear surface of the brush portion 3.

Here, the electrostatic capacitances C1 and C2 are approximately several hundred pF. On the other hand, the electrostatic capacitance C3 is several pF, which is an extremely small value compared to the capacitances C1 and C2 with the ground. Meanwhile, none of the electrostatic capacitances C1 through C3 are stable, and instead fluctuate depending on changes in the surrounding environment. However, because changes in the electrostatic capacitance C3 are extremely low compared to C1 and C2, changes in C3 have a much greater effect on changes in the combined capacitance Cx than do changes in C1 or C2. Therefore, in the present variation, the state of contact with the body is determined by detecting changes in the combined capacitance Cx as changes in the electrostatic capacitance C3.

In the present variation, changes in the combined capacitance Cx are detected as changes in a frequency by the detection portion 55 converting the combined capacitance Cx into a frequency. Changes in the combined capacitance Cx are inputted into the CPU 120 from the detection portion 55 as inverter counter outputs (H level or L level outputs). Note that this configuration is merely an example, and the configuration for detecting changes in the combined capacitance Cx may employ other configurations known from the past.

According to the present variation, the state of contact can be detected using a single electrode, which makes it possible to simplify the configuration of the electric toothbrush.

Note that the electric toothbrush according to the aforementioned fourth embodiment and the present variation may employ another electrode (conductor) configuration, such as that disclosed in JP-2009-222704A, which detects contact between an electric thermometer and a human body.

Second Variation

The electrostatic capacitance-type sensor may be configured as what is known as a touch sensor. For example, the electrostatic capacitance-type sensor may be a surface-type electrostatic capacitance-type sensor that includes a clear conductive film and four corner electrodes.

In this case, the electrode portion 53 includes the conductive film and four electrodes. When the panel surface makes contact with or approaches the body, the conductive film enters the same state as if it was routed through a capacitor, and thus a current flows through the body. The detection portion 55 according to the present variation detects this current and outputs the result of the detection to the CPU 120, The CPU 120 obtains the detected current amount and determines whether or not contact is being made with the body by detecting changes in the electrostatic capacitance. The CPU 120 can determine that contact is being made with the body if, for example, the obtained current amount is greater than or equal to a threshold set in advance through experimentation.

Fifth Embodiment

Although the first through fourth embodiments improve the precision of area detection by providing a contact detection unit in the electric toothbrush, in the present embodiment, an infrared sensor for detecting temperatures is provided on the brush surface of the electric toothbrush in order to detect whether the teeth or the gums are being brushed.

The basic configuration and operations of the electric toothbrush according to the present embodiment are the same as those in the first embodiment. Accordingly, the following will describe in detail only the differences from the first embodiment.

Figure 43:
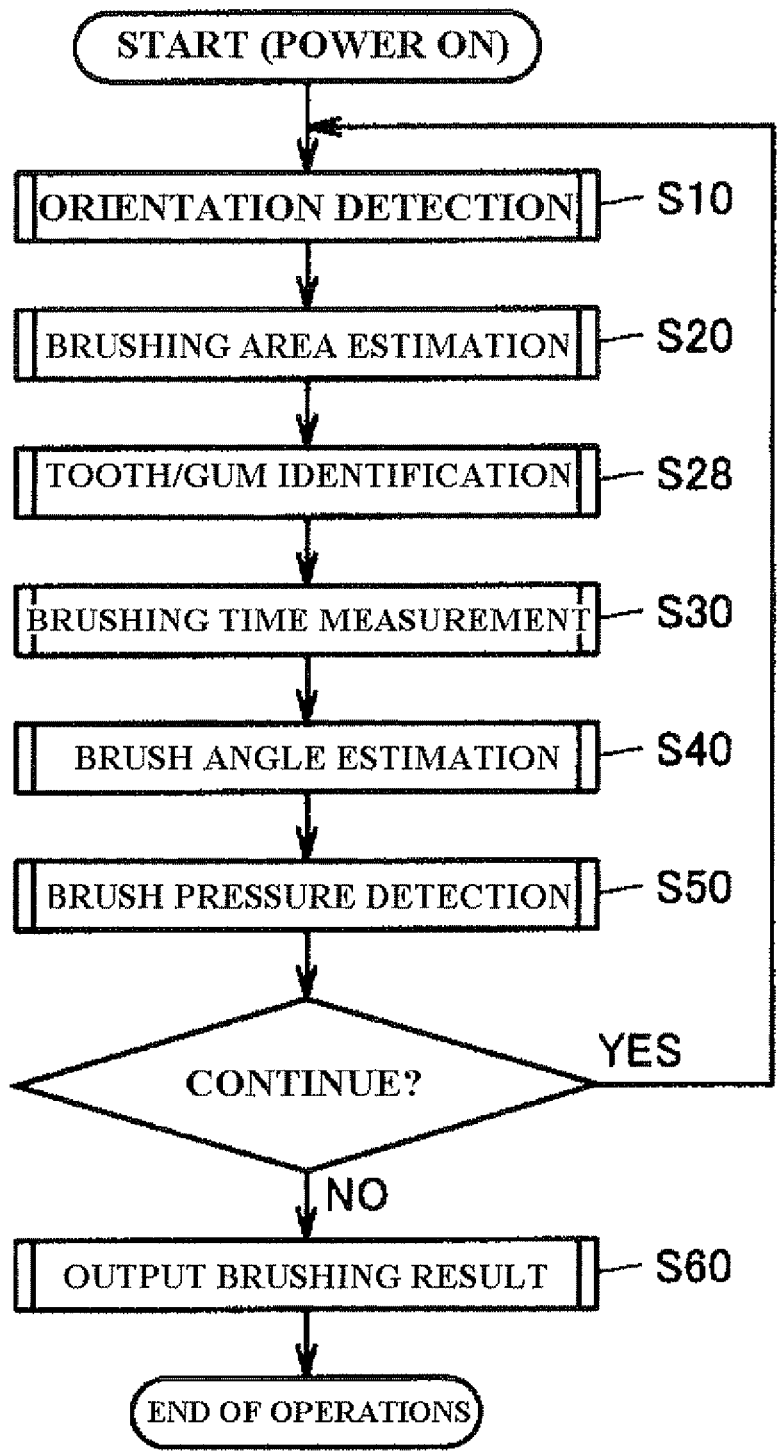
FIG. 43 is a flowchart illustrating a brushing evaluation process according to a fifth embodiment.

FIG. 43 is a flowchart illustrating a brushing evaluation process according to the fifth embodiment.

As shown in FIG. 43, the only difference between this embodiment and the first embodiment is that a tooth/gum identification process (S28) is inserted between the brushing area estimation process (S20) and the brushing time measurement process (S30).

Figure 44:
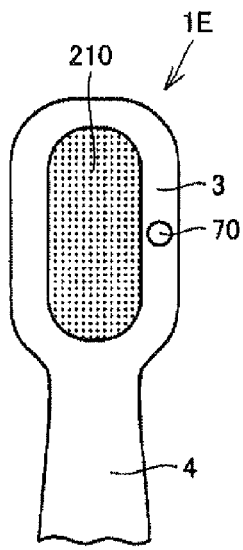
FIG. 44 is a diagram partially illustrating an example of the external appearance of an electric toothbrush according to the fifth embodiment.

FIG. 44 is a perspective view illustrating an example of the external appearance of an electric toothbrush 1E according to the fifth embodiment.

As shown in FIG. 44, the electric toothbrush 1E is provided, in the brush surface of the brush portion 3, with an infrared sensor 70 such as a thermopile. The location in which the infrared sensor 70 is disposed is not limited to the location shown in FIG. 44, and may be anywhere on the brush surface.

Note that it is assumed in the present embodiment that, as in the first embodiment or the fourth embodiment, the rear surface electrode 521 or the electrostatic capacitance-type sensor 53 is provided on the rear surface of the brush portion 3.

Figure 45:
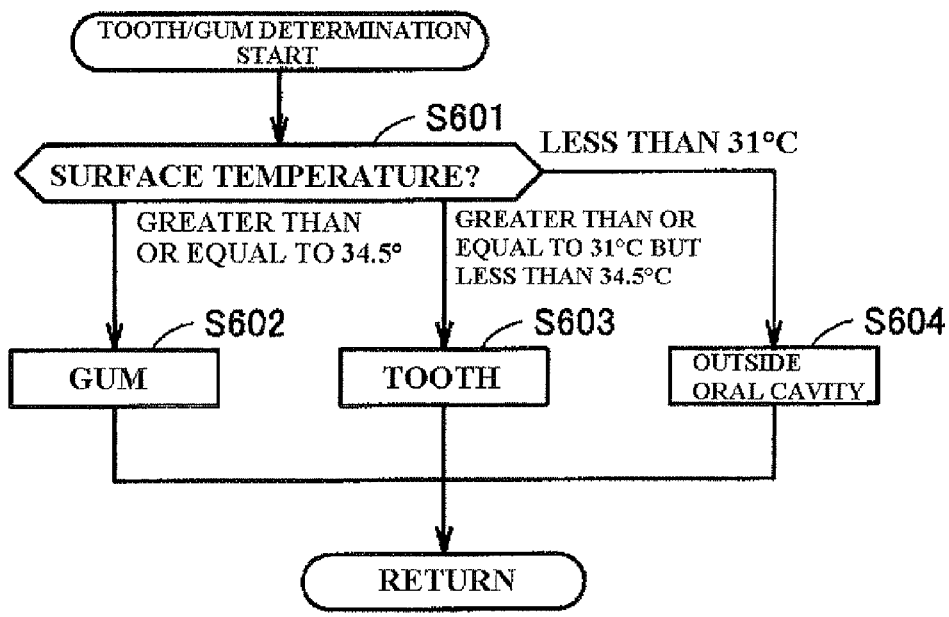
FIG. 45 is a flowchart illustrating a tooth/gum identification process according to the fifth embodiment.

FIG. 45 is a flowchart illustrating the tooth/gum identification process (S28).

As shown in FIG. 45, the CPU 120 detects a surface temperature obtained from the infrared sensor 70 for each of the estimated areas (S601). If the surface temperature is greater than or equal to a first threshold (for example, 34.5° C.), it is determined that the brush surface is facing the gums (S602). Meanwhile, if the surface temperature is less than the first threshold but greater than or equal to a second threshold (for example, 31° C.), it is determined that the brush surface is facing the teeth (S603). If the surface temperature is less than the second threshold, it is determined that the toothbrush is outside of the oral cavity (S604).

In this manner, the brushing time for teeth and the brushing time for gums can be outputted separately by differentiating between the teeth and areas aside from the teeth. Accordingly, the output of brushing results can be made more useful in the prevention of cavities, periodontal disease, and so on.

Sixth Embodiment

Although the first through fourth embodiments describe improving the precision of area detection by providing a contact detection unit in the electric toothbrush, in the present embodiment, optical sensors are provided on both the front surface side (the brush side) and the rear surface side of the shank portion in the electric toothbrush in order to correct errors in determinations between front teeth and back teeth. This is because when the electric toothbrush is in a horizontal orientation, there are cases where it is difficult to differentiate between front teeth and back teeth using only the output of the accelerometer.

The basic configuration and operations of the electric toothbrush according to the present embodiment are the same as those in the first embodiment. Accordingly, the following will describe in detail only the differences from the first embodiment.

Figure 46:
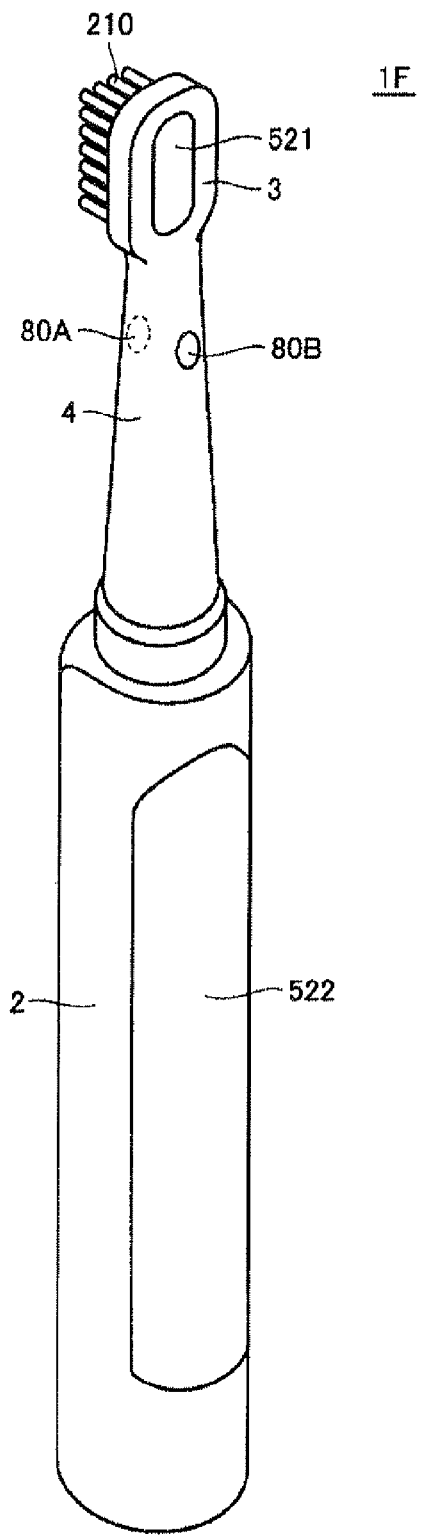
FIG. 46 is a perspective view illustrating an example of the external appearance of an electric toothbrush according to a sixth embodiment.

FIG. 46 is a perspective view illustrating an example of the external appearance of an electric toothbrush 1F according to the sixth embodiment.

As shown in FIG. 46, optical sensors 80A and 80B for detecting brightnesses are provided in the shank portion 4 of the electric toothbrush 1F, in locations in the vicinity of the brush portion 3. Components that have a function for converting light into electricity, such as photodiodes or phototransistors, can be employed as the optical sensors 80A and 80B.

The optical sensor 80A is provided on the front surface side of the shank portion 4, whereas the optical sensor 80B is provided on the rear surface side of the shank portion 4. Note that the optical sensors 80A and 80B are not limited to the locations illustrated in FIG. 46, as long as the optical sensors 80A and 80B are provided in locations that enter into the mouth when brushing the back teeth. For example, the optical sensors 80A and 80B may be provided in locations of the brush portion 3 that are in the vicinity of the shank portion 4.

The flow of the brushing evaluation process according to the present embodiment may be the same as that described in the third embodiment and illustrated in FIG. 33. In the present embodiment, however, the following process is carried out in S26 (the area correction process) of FIG. 33.

First, the CPU 120 determines whether the optical sensors 80A and 80B are in an active state or in an inactive state. Specifically, it is determined whether or not the outputs of the optical sensors 80A and 80B are greater than or equal to a predetermined threshold; if the outputs are greater than or equal to the threshold, it is determined that the optical sensors are in the active state (that is, that it is bright), whereas if the outputs are less than the threshold, it is determined that the optical sensors are in the inactive state (that is, that it is dark).

The brushing area is determined to be the front teeth if only one of the optical sensors 80A and 80B is in the active state. Specifically, if only the optical sensor 80A, which is disposed on the front surface side, is in the active state, the front surface side is facing toward the outside of the mouth, and it is thus determined that the front teeth on the lingual side or the palatal side are being brushed. On the other hand, if only the optical sensor 80B, which is disposed on the rear surface side, is in the active state, the rear surface side is facing toward the outside of the mouth, and it is thus determined that the front teeth on the labial side are being brushed.

However, if both of the optical sensors 80A and 80B are in the inactive state, it is estimated that both of the optical sensors are within the oral cavity, and it is thus determined that the brushing area corresponds to the back teeth. On the other hand, if both of the optical sensors 80A and 80B are in the active state, it is determined that neither the front teeth nor the back teeth are being brushed and that the brush portion 3 is outside of the oral cavity.

If the determination results for the front teeth/back teeth as described thus far differ from the determination results for the front teeth/back teeth from the previous brushing area estimation process, the brushing area is corrected in accordance with the new determination results. However, if the determination results for the front teeth/back teeth from the area correction process match the determination results for the front teeth/back teeth from the previous brushing area estimation process, the process ends without corrections being made.

In this manner, by employing the optical sensors 80A and 80B, brushing areas can be estimated with a high level of precision, even in the case where there is an error in the brushing area determined using the accelerometer 15.

In this manner, the embodiments and variations disclosed herein are to be understood in all ways as exemplary and in no ways limiting. The technical scope of the present invention is defined by the appended claims, and all variations that fall within the meaning and range of equivalency of the claims are intended to be embraced therein.

REFERENCE SIGNS LIST 1, 1A, 1B, 1C, 1D, 1E Electric Toothbrush
2 Main Body Portion
3 Brush Portion
4 Shank Portion
5 Vibrating Member
10 Motor
11 Rotating Shaft
12 Driving Circuit
13 Chargeable Battery
14 Coil
15 Accelerometer
17 Load Sensor
20 Stem Portion
21 Brush Component
30 Eccentric Shaft
50 Contact Detection Unit
52 Electrode Portion
53 Electrostatic Capacitance-type Sensor
54 Detection Portion
61, 62, 63 Electrode
64, 65 Lead Wire
70 Infrared Sensor
80A, 80B Optical Sensor
100 Charger
110 Display Device
111 Display
112 Data Receiving Unit
120 CPU
121 Memory
122 Timer
123 Data Transmission Unit
202 Elastic Member
203 Shaft Bearing
210 Bristles
521, 522, 523A, 523B, 523C, 524, 525A, 525B Electrode
S Switch

The invention claimed is:

1. An electric toothbrush comprising:
bristles;
a driving unit for driving the bristles;
an orientation detection sensor for detecting the orientation of the electric toothbrush; and
an electrode-based contact detection unit for detecting contact with a body,
wherein the contact detection unit includes a first detection unit for detecting contact with or proximity to a rear surface side of a brush portion in which the bristles are disposed;
the electric toothbrush further comprises:
a detection unit for detecting orientation information of the electric toothbrush based on an output from the orientation detection sensor; and
an area estimation unit for estimating a brushing area based on at least the orientation information, and
wherein the area estimation unit includes a determination unit for determining, in the case where the brushing area determined based on the orientation information is a dentition surface on a right buccal side or a left lingual side or a dentition surface on a left buccal side or a right lingual side, whether the brushing area corresponds to the buccal side or the lingual side based on an electric signal obtained from the first detection unit, and
wherein the first detection unit includes an electrode disposed on the rear surface side of the brush portion, the electrode defining an electric passage with respect to the body when the electrode is brought into contact with or in a vicinity of the body.

2. The electric toothbrush according to claim 1,
wherein the determination unit calculates the percentage of time for which the rear surface side of the brush portion is in contact with the body based on the output of the first detection unit, and determines that the brushing area corresponds to the buccal side if the calculated percentage of time is greater than or equal to a predetermined percentage and determines that the brushing area corresponds to the lingual side if the calculated percentage of time is less than the predetermined percentage.

3. The electric toothbrush according to claim 1,
wherein
the determination unit determines whether or not contact is made with the body by detecting the magnitude of the impedance of the electrode.

4. The electric toothbrush according to claim 1,
wherein the first detection unit further includes an electrode disposed on a main body portion of the electric toothbrush.

5. The electric toothbrush according to claim 1,
wherein the first detection unit includes an electrostatic capacitance-type detection unit, that contains an electrode, disposed on the rear surface side of the brush portion; and
the determination unit determines contact with or proximity to the body by detecting changes in the electrostatic capacitance of the electrostatic capacitance-type detection unit.

6. The electric toothbrush according to claim 1,
wherein the contact detection unit further includes a second detection unit for detecting contact with a location that is not the rear surface of the brush portion but is a location that can enter into the mouth during brushing; and the electric toothbrush further comprises:
a detailed area detection unit for detecting, based on an electrical signal obtained from the second detection unit, a more detailed area than the brushing area estimated by the area estimation unit.

7. The electric toothbrush according to claim 6,
wherein the second detection unit detects contact with a shank portion; and
the detailed area detection unit detects, in the case where the estimated brushing area corresponds to the back teeth, a detailed area of the back teeth by detecting whether or not the second detection unit has come into contact with the body.

8. The electric toothbrush according to claim 6,
wherein the second detection unit detects contact with the tip of the brush portion; and
the detailed area detection unit detects, in the case where the estimated brushing area corresponds to the front teeth, a detailed area of the front teeth by detecting whether or not the second detection unit has come into contact with the body.

9. The electric toothbrush according to claim 1,
wherein the contact detection unit further includes a second detection unit for detecting contact with a side surface of the brush portion; and the electric toothbrush further comprises:
an area correction unit for correcting, based on an electrical signal obtained from the second detection unit, the brushing area estimated by the area estimation unit.

10. The electric toothbrush according to claim 1, further comprising:
an infrared sensor, disposed on the brush surface of the brush portion, for detecting a temperature; and
an identification unit for identifying, based on an output from the infrared sensor, whether the teeth or the gums are being brushed.

11. The electric toothbrush according to claim 1, further comprising:
an optical sensor provided in a location that enters into the oral cavity when brushing the back teeth; and
an area correction unit for correcting the brushing area estimated by the area estimation unit by determining whether the area being brushed corresponds to front teeth or back teeth based on a signal obtained from the optical sensor.

12. The electric toothbrush according to claim 1, further comprising:
a measurement unit for measuring a brushing time for each brushing area estimated by the area estimation unit; and
an output unit for outputting a brushing result based on a result of measuring the brushing time.

13. The electric toothbrush according to claim 1, further comprising:
a mode switching unit for switching an operating mode of the driving unit in accordance with the brushing area estimated by the area estimation unit.

* * * * *